US011207346B2

(12) United States Patent
Martin-Tereso Lopez et al.

(10) Patent No.: US 11,207,346 B2
(45) Date of Patent: Dec. 28, 2021

(54) AQUEOUS COMPOSITION FOR LIVESTOCK ANIMALS

(71) Applicant: Nutreco Nederland B.V., Boxmeer (NL)

(72) Inventors: Javier Martin-Tereso Lopez, Nijmegen (NL); Isabela Pena Carvalho De Carvalho, Nijmegen (NL)

(73) Assignee: Nutreco Nederland B.V., Boxmeer (NL)

(*) Notice: Subject to any disclaimer, the term of this patent is extended or adjusted under 35 U.S.C. 154(b) by 263 days.

(21) Appl. No.: 16/306,404

(22) PCT Filed: Jun. 7, 2017

(86) PCT No.: PCT/NL2017/050376
§ 371 (c)(1),
(2) Date: Nov. 30, 2018

(87) PCT Pub. No.: WO2017/213502
PCT Pub. Date: Dec. 14, 2017

(65) Prior Publication Data
US 2020/0316106 A1  Oct. 8, 2020

(30) Foreign Application Priority Data
Jun. 7, 2016  (NL) .................................... 2016909

(51) Int. Cl.
*A61K 33/00*    (2006.01)
*A23K 20/142*   (2016.01)
(Continued)

(52) U.S. Cl.
CPC ............ *A61K 33/00* (2013.01); *A23K 20/142* (2016.05); *A23K 20/163* (2016.05); *A23K 20/22* (2016.05);
(Continued)

(58) Field of Classification Search
CPC ...... A23K 50/75; A23K 50/10; A23K 20/142; A23K 20/22; A23K 20/10; A23K 20/163;
(Continued)

(56) References Cited

U.S. PATENT DOCUMENTS 3,241,974 A   3/1966 Seiden
5,089,477 A   2/1992 Fregly et al.
(Continued)

FOREIGN PATENT DOCUMENTS

WO   2004/047553 A1   6/2004

OTHER PUBLICATIONS

Liquid Supplements posted Jan. 2001 (https://www.noble.org/news/publications/ag-news-and-views/2001/january/liquid-supplements/) (Year: 2001).*

(Continued)

*Primary Examiner* — Blessing M Fubara
(74) *Attorney, Agent, or Firm* — Foley & Lardner LLP; Sunit Talapatra

(57) ABSTRACT

Aqueous compositions and methods using the compositions for preventing or minimizing live body weight loss in livestock animals subjected to a prolonged period of feed deprivation, e.g., such as during the period before slaughter or during a period surrounding transportation from one location to another location (e.g., before, during and/or after), and/or for minimizing carcass weight loss or carcass yield loss, and/or meat quality deterioration and/or for preventing or minimizing deterioration of the well-being or health of livestock animals subjected to a prolonged period of feed deprivation, e.g., such as during the period before slaughter or during a period surrounding transportation from one location to another location (e.g., before, during and/or after).

28 Claims, 5 Drawing Sheets

(51) Int. Cl.
*A23K 20/163* (2016.01)
*A23K 20/22* (2016.01)
*A23K 20/24* (2016.01)
*A23K 50/10* (2016.01)
*A61K 9/08* (2006.01)
*A61K 31/19* (2006.01)
*A61K 31/198* (2006.01)
*A61K 31/7004* (2006.01)
*A61K 33/04* (2006.01)
*A61K 33/06* (2006.01)
*A61K 33/42* (2006.01)

(52) U.S. Cl.
CPC .............. *A23K 20/24* (2016.05); *A23K 50/10* (2016.05); *A61K 9/08* (2013.01); *A61K 31/19* (2013.01); *A61K 31/198* (2013.01); *A61K 31/7004* (2013.01); *A61K 33/04* (2013.01); *A61K 33/06* (2013.01); *A61K 33/42* (2013.01)

(58) Field of Classification Search
CPC ........ A61K 33/04; A61K 31/19; A61K 33/42; A61K 33/00; A61K 31/7004; A61K 9/08; A61K 33/06; A61K 31/198
See application file for complete search history.

(56) References Cited

U.S. PATENT DOCUMENTS

| | | | | |
|---|---|---|---|---|
| 5,505,968 | A * | 4/1996 | Schaefer | A23K 20/147 424/617 |
| 6,299,913 | B1 * | 10/2001 | Block | A23K 20/20 426/2 |
| 2002/0110621 | A1 * | 8/2002 | Robergs | A23L 2/00 426/74 |
| 2005/0095271 | A1 * | 5/2005 | Mathewson | A23L 33/175 424/439 |
| 2007/0154614 | A1 * | 7/2007 | Sherwood | A23L 3/3409 426/583 |

OTHER PUBLICATIONS

International Search Report and Written Opinion received for PCT Patent Application No. PCTNL2017/050376, dated Jul. 27, 2017, 12 pages.
Search Report and Written Opinion received for Patent Application No. NL2016909, dated Jan. 12, 2017, 11 pages.

* cited by examiner

AQUEOUS COMPOSITION FOR LIVESTOCK ANIMALS

CROSS-REFERENCE TO RELATED APPLICATIONS

This application is a national phase entry under 35 U.S.C. § 371 of International Patent Application PCT/NL2017/050376, filed Jun. 7, 2017, designating the United States of America and published in English as International Patent Publication WO 2017/213502 A1 on Dec. 14, 2017, which claims the benefit under Article 8 of the Patent Cooperation Treaty to The Netherlands Patent Application Serial No. 2016909, filed Jun. 7, 2016.

TECHNICAL FIELD

This application is in the field of livestock liquid supplements and methods thereof for preventing or minimizing live body weight loss in livestock animals subjected to a prolonged period of feed deprivation, e.g., such as during the period before slaughter or during a period surrounding transportation from one location to another location (e.g., before, during and/or after), and/or for minimizing carcass weight loss or carcass yield loss, and/or meat quality deterioration and/or for preventing or minimizing deterioration of the well-being or health of livestock animals subjected to a prolonged period of feed deprivation, e.g., such as during the period before slaughter or during a period surrounding transportation from one location to another location (e.g., before, during and/or after).

BACKGROUND

During the pre-slaughter period or during and/or after transportation from one location to another location, livestock animals (e.g., cattle, beef, poultry, etc.) are exposed to a range of challenging stimuli including handling stress, transport stress, changes in social structure (separation and mixing of groups), and feed deprivation. These stimuli, alone or in combination, may lead to loss of live body weight, which often translates into a lower carcass weight or yield and/or poor meat quality (e.g., after slaughter of the animal) or may jeopardize the well-being or health of the animal (e.g., if not slaughtered).

Large efforts have been devoted to develop strategies for preventing or mitigating the negative effects of handling stress, transport stress, and/or feed deprivation in livestock animals, particularly during the pre-slaughter period or during periods surrounding transportation from one location to another location (e.g., before, during and/or after transportation). Such strategies mainly involve manipulating pre-slaughter nutrition and electrolyte management or manipulating nutrition and electrolyte surrounding periods of transportation from one location to another location (e.g., before, during and/or after transport). In this respect, several feed supplements largely consisting of a mixture of electrolytes and amino acids have been developed. For instance, U.S. Pat. No. 5,505,968 describes nutrient supplement for livestock consisting of one or more sources of certain electrolytes (e.g., sodium, potassium and magnesium), one or more sources of certain amino acids, e.g., alanine, lysine, phenylalanine, methionine, threonine, leucine, isoleucine, valine, tryptophan and glutamate and optionally one or more sources of energy (e.g., glucose).

WO2004/047553 discloses a supplement for livestock animals comprising electrolytes selected from the group consisting of calcium, manganese, magnesium, potassium, and amino acids such as glycine and aspartic acid, and optionally vitamins B, C and E, arginine, histidine and cysteine, and trace minerals chromium, selenium, calcium, copper, iron and zinc.

However, the electrolytes-based feed supplements described above are not optimal because such feed supplements are often reported to be ineffective at alleviating or preventing the negative effects of handling stress transport stress, and/or feed deprivation in livestock animals, such as during the pre-slaughter period or during periods surrounding transportation from one location to another location (e.g., before, during and/or after transportation) and/or ineffective at preventing or minimizing live body weight loss, and/or carcass weight loss as well as poor meat quality as a result of prolonged feed deprivation, such as for instance during the pre-slaughter period or are ineffective at preventing or minimizing feed deprivation-induced effects on the well-being or health of livestock animals during periods surrounding transportation from one location to another location (e.g., before, during and/or after transportation).

Therefore, there is a need for compositions or improved compositions for livestock animals (e.g., beef, poultry, such as broiler chickens) and methods using the compositions, which are devoid of at least one of the limitations mentioned above, and that are suitable for preventing or minimizing live body weight loss occurring as a result of feed deprivation, e.g., such as during the pre-slaughter period or during periods surrounding transportation from one location to another location (e.g., before, during and/or after transportation), and/or that are suitable for preventing or minimizing feed deprivation-induced carcass weight loss and/or carcass yield loss and/or meat quality deterioration post slaughter or that are suitable for preventing or minimizing feed deprivation-induced effects on the well-being or health of livestock animals during periods surrounding transportation from one location to another location (e.g., before, during and/or after transportation) (dc).

BRIEF SUMMARY

In a first aspect, an aqueous composition for a livestock animal comprising potassium and sodium is disclosed, wherein the potassium to sodium ratio is in the range of about 65:35 to about 95:05, and wherein the composition is hypotonic or isotonic.

In an embodiment, the composition as taught herein may further comprise one or more electrolytes selected from magnesium, calcium, chloride, bicarbonate, acetate, propionate, sulphate and phosphate.

In an embodiment, the composition as taught herein may further comprise one or more gluconeogenic precursor.

In an embodiment, the gluconeogenic precursor may be selected from glycerol, propylene glycol, dextrose, lactate, a glucogenic amino acid, and sugar, and may preferably be glycerol.

In an embodiment, the glucogenic amino acid may be selected from alanine, glutamine, glycine, serine, valine, histidine, arginine, cysteine, proline, glutamate, aspartate, asparagine, methionine, phenylalanine, isoleucine, threonine, tyrosine and tryptophan.

In a preferred embodiment, the amino acid may be selected from alanine and glutamine.

In an embodiment, the sugar may be selected from sucrose and maltose.

In an embodiment, the composition as taught herein may further comprise an alkalinizing agent.

In an embodiment, the alkalinizing agent may be selected from propionate, bicarbonate, citrate, carbonate, lactate and may preferably be acetate and/or propionate anions.

In an embodiment, the livestock animal may be selected from ruminants and monogastric animals.

In an embodiment, the ruminant may be selected from bovine, ovine and caprine, may preferably be bovine (e.g., beef).

In an embodiment, the monogastric animal may be selected from poultry, swine, horses, and may preferably be poultry (e.g., broiler chicken).

In a further aspect, a concentrate suitable for the preparation of the composition as taught herein is disclosed that, when diluted in water, provides a composition as taught herein.

In an embodiment, the concentrate as taught herein may be about 5 to 30 times, preferably about 20 times, more concentrated that the composition as taught herein.

In a further aspect, a method for preventing or minimizing live body weight loss in livestock animals subjected to feed deprivation is disclosed, comprising the step of:
administering to the livestock animal an effective amount of an aqueous composition comprising potassium and sodium, wherein the potassium to sodium ratio is in the range of about 65:35 to about 95:05, and wherein the composition is hypotonic or isotonic, at the onset of and/or during a period of feed deprivation and/or after a period of feed deprivation has been ended.

In an embodiment, the period of feed deprivation may be about 0.05 to 72 hours, preferably about 1 to 48 hours, e.g., about 5 to 72 hours or about 12 to 48 hours.

In a preferred embodiment, the period of feed deprivation may be prior to slaughter or prior transportation from one location to another location or during transportation from one location to another location.

In a further aspect, a method for minimizing carcass weight loss and/or for minimizing meat quality deterioration is disclosed comprising the step of:
administering a livestock animal with an effective amount of an aqueous composition comprising potassium and sodium, wherein the potassium to sodium ratio is in the range of about 65:35 to about 95:05, and wherein the composition is hypotonic or isotonic, within a period of about 5 to about 72 hours, preferably about 12 to about 48 hours prior to slaughter or within a period of about 0.05 to about 72 hours, preferably about 1 to about 48 hours prior to transportation from one location to another location; or within about 0.05 to about 72 hours, preferably about 1 to about 48 hours after transportation from one location to another location; or within a period during transportation from one location to another location.

In a further aspect, a method for preventing or minimizing deterioration of the well-being or health of a livestock animal is disclosed comprising the step of:
administering to the livestock animal an effective amount of an aqueous composition comprising potassium and sodium, wherein the potassium to sodium ratio is in the range of about 65:35 to about 95:05, and wherein the composition is hypotonic or isotonic, within a period of about 0.05 to about 72 hours, preferably about 1 to about 48 hours prior to transportation from one location to another location; or within a period of about 0.05 to about 72 hours, preferably about 1 to about 48 hours after transportation from one location to another location; or within a period during transportation from one location to another location.

In an embodiment, the livestock animal may be selected from ruminants and monogastric animals.

In an embodiment, the ruminant may be selected from bovine, ovine and caprine, and may preferably be bovine (e.g., beef).

In an embodiment, the monogastric animal may be selected from poultry, swine, horses, and may preferably be poultry (e.g., broiler chickens).

In an embodiment relating to the methods as taught herein, the composition may further comprise one or more electrolytes selected from magnesium, calcium, chloride, bicarbonate, acetate, propionate, sulphate and phosphate.

In an embodiment relating to the methods as taught herein, the composition may further comprise one or more gluconeogenic precursor.

In an embodiment relating to the methods as taught herein, the gluconeogenic precursor may be selected from glycerol, propylene glycol, dextrose, lactate, a glucogenic amino acid, and sugar, and preferably is glycerol.

In an embodiment relating to the methods as taught herein, the glucogenic amino acid may be selected from alanine, glutamine, glycine, serine, valine, histidine, arginine, cysteine, proline, glutamate, aspartate, asparagine, methionine, phenylalanine, isoleucine, threonine, tyrosine and tryptophan.

In an embodiment relating to the methods as taught herein, the glucogenic amino acid may be selected from alanine and glutamine.

In an embodiment relating to the methods as taught herein, the sugar may be selected from sucrose and maltose.

In an embodiment relating to the methods as taught herein, the composition may further comprise an alkalinizing agent.

In an embodiment relating to the methods as taught herein, the alkalinizing agent may be selected from propionate, bicarbonate, citrate, carbonate, lactate and preferably acetate and/or propionate anions.

General Definitions

In the following description and examples, a number of terms are used. In order to provide a clear and consistent understanding of the specification and claims, including the scope to be given to such terms, the following definitions are provided. Unless otherwise defined herein, all technical and scientific terms used have the same meaning as commonly understood by one of ordinary skill in the art to which this disclosure belongs. The disclosures of all publications, patent applications, patents and other references are incorporated herein in their entirety by reference.

The term "electrolyte(s)" as used herein refers to a substance that produces an electrically conducting solution when dissolved in a polar solvent, such as water. The dissolved electrolyte separates into cations and anions, which disperse uniformly through the solvent. If an electrical potential (voltage) is applied to such a solution, the cations of the solution would be drawn to the electrode that has an abundance of electrons, while the anions would be drawn to the electrode that has a deficit of electrons. The movement of anions and cations in opposite directions within the solution amounts to a current. This includes most soluble salts, acids, and bases. In physiology, the primary ions of electrolytes are sodium ($Na^+$), potassium ($K^+$), calcium ($Ca_2^+$), magnesium ($Mg_2^+$), chloride (CF), hydrogen phosphate ($HPO_4^{2-}$), and hydrogen carbonate (also referred to as bicarbonate) ($HCO_3^-$), acetate ($CH_3CO_2^-$), propionate ($C_2H_5COO^-$), sulphate ($SO_4^{-2}$), and phosphate (PO$_4^{-3}$). Electrolytes are usually provided in the form of a salt. Sodium is the main electrolyte found in extracellular fluid and potassium is the main intracellular electrolyte; both are involved in fluid balance and blood pressure control. Magnesium ions interact with polyphosphate compounds such as ATP, DNA, and RNA. Hundreds of enzymes require magnesium ions to function. Living animals (including humans) require a subtle and complex electrolyte balance between the intracellular and extracellular environment. In particular, the maintenance of precise osmotic gradients of electrolytes is important, i.e., are critical for nerve and muscle function. Electrolyte solutions are normally formed when a salt is placed into a solvent, such as water, and the individual components dissociate due to the thermodynamic interactions between solvent and solute molecules, in a process called solvation. For example, when table salt (sodium chloride), NaCl, is placed in water, the salt (a solid) dissolves into its component ions, according to the dissociation reaction: NaCl(s)→Na$^+$(aq)+Cl$^-$(aq). Under normal conditions, electrolyte balance is regulated by hormones, in general with the kidneys flushing out excess levels. In humans and animals, electrolyte homeostasis is regulated by hormones such as antidiuretic hormone, aldosterone and parathyroid hormone. Under pathological or disease states (diarrhea, vomiting, anorexia, bulimia and others), electrolyte homeostasis may be regulated by oral, or in emergencies, intravenous intake of electrolyte-containing substances. If no treated or restored, serious electrolyte disturbances may lead to cardiac and neurological complications.

The term "livestock animal(s)," as used herein, refers to domesticated animals raised in an agricultural setting for commercial purposes (e.g., meat, wool, milk, etc.). The term "livestock animal(s)" encompasses cattle (e.g., beef), sheep, goats, swine, poultry (including egg-producing poultry or broiler chickens), and equine animals used for food. A livestock animal may be a ruminant (e.g., bovine (beef), ovine, or caprine) or a monogastric animal (e.g., swine, horse, or poultry).

The term "ruminants" or "ruminant animals," as used herein, refers to mammals that are able to acquire nutrients from plant-based food through fermentation in a specialized stomach chamber prior to digestion, principally through bacterial actions. The process typically requires regurgitation of fermented ingesta (known as cud), and chewing it again. The process of rechewing the cud to further break down plant matter and stimulate digestion is called "rumination." The primary difference between ruminant animals and non-ruminant animals (e.g., monogastric animal) is that ruminant animals have a four-chambered stomach. Non-limiting examples of ruminants include bovine animals such as beef cattle, sheep, goats, buffalo, moose, elks, bison, giraffes, yak, deer, antelopes, dairy cattle, and the like.

The term "monogastric animal(s)," as used herein, refers to an animal having a simple single-chambered stomach, compared with a ruminant organism, like a beef, cow, goat, or sheep, which has a four-chambered complex stomach. Examples of monogastric animals include omnivores such as humans, rats, dogs and pigs, and carnivores such as cats, and herbivores such as horses and rabbits.

The term "bovine animals" or "bovine," as used herein, refers to a variety of bovine animals including cows, bulls (beef), steers, stags, heifers, calves, oxen, and the like. In this disclosure, bovine animals include both domestic and wild bovine animals and male and female bovine animals (particularly growing animals). Bovine animals may be of the genus *Bos*, e.g., the species *Bos taurus, Bos indicus*, or the like.

The term "ovine animals" or "ovine," as used herein, refers to animals belonging to the *Ovis* genus of mammals, which is part of the goat-antelope subfamily of the ruminant family Bovidae. Non-limiting examples of ovine animals include sheep, mouflon, urial, and the like. In this disclosure, ovine animals include both domestic and wild ovine animals and male and female ovine animals (particularly growing animals).

The term "caprine animals" or "caprine," as used herein, refers to animals belonging to the *Capra* genus of mammals, which is part of the Caprinae subfamily of the ruminant family Bovidae. Non-limiting examples of caprine animals include goat, ibex, markhor and the like. In this disclosure, caprine animals include both domestic and wild caprine animals and male and female caprine animals (particularly growing animals).

The term "feed deprivation," as used herein, refers to a prolonged period of time where a livestock animal does not eat any feed or food or does not receive any feed or does not have access to feed or any substance containing nutrients, such as carbohydrates, proteins, and fats, that can be ingested by a living organism and metabolized into energy and body tissue. A livestock animal may be forced subjected to a period of feed deprivation, for instance, such as during the pre-slaughter period, or during a period surrounding transportation from one location to another location (e.g., before, during and/or after) or may be feed deprived as a result of illness or stress or (voluntary) refusal to eat feed. In this disclosure, the term "a period of feed deprivation" refers to a period of time in the range of about 0.5 hour to about 72 hours, for instance, about 1 hour to about 72 hours, about 10 to about 70 hours, about 15 to about 65 hours, about 20 to about 60 hours, about 25 to about 55 hours, about 30 to about 50 hours, or about 35 to about 45 hours, preferably about 12 hours to 48 hours, for instance, about 16 to about 44 hours, about 20 to about 40 hours, about 24 to about 36 hours, or about 28 to about 32 hours during which a livestock animal does not eat or does not receive or does not have access to feed. Non-limiting consequence(s) of feed deprivation include loss of live body weight, loss of carcass weight and/or poor meat quality as well as deterioration of the well-being or health of a livestock animal.

The term "pre-slaughter period" or "period prior to slaughter," as used herein, refers to a period of time in the range of about 5 hours to about 72 hours, for instance, 10 to 70 hours, 15 to 65 hours, 20 to 60 hours, 25 to 55 hours, 30 to 50 hours, or 35 to 45 hours, preferably about 12 hours to 48 hours, for instance, 16 to 44 hours, 20 to 40 hours, 24 to 36 hours, or 28 to 32 hours prior to the slaughter of a livestock animal. During this period, livestock animals destined for slaughter may be transported from one location to another location. Prior transport, livestock animals typically do not have access to feed but usually have access to water. During transport, livestock animals typically do not have access to feed and may or may not have access to water (usually not). The term "pre-slaughter period" may also include a post-transport period, wherein the livestock animals are maintained at the other location (e.g., the slaughter house) for a certain time, for instance, 2 to 36 hours, 5 to 30 hours, 8 to 28 hours or 12 to 24 hours, prior to slaughter. During this period, livestock animals typically do not have access to feed but have access to water. The term "pre-slaughter period" also includes instances where the livestock animals are not transported to another location before slaughter but remain where they are or are moved to a different pen or paddock in the same property. Typically, livestock animals may be held in this location for a certain time, for instance, 2 to 36 hours, 5 to 30 hours, 8 to 28 hours or 12 to 24 hours, prior slaughter and do not have access to feed but usually have access to water during this period.

The term "during periods surrounding transportation" as used herein refers to periods before, during or after transportation of a livestock animal from one location to another location. The term "period before transportation" or "pre-transportation period" refers to a period of time in the range of about 0.05 hour to about 72 hours, for instance, about 1 hour to about 72 hours, about 5 to about 70 hours, about 10 to about 65 hours, about 20 to about 60 hours, about 25 to about 55 hours, about 30 to about 50 hours, or about 35 to about 45 hours, preferably about 12 hours to about 48 hours, for instance, about 16 to about 44 hours, about 20 to about 40 hours, about 24 to about 36 hours, or about 28 to about 32 hours prior to transporting a livestock animal from one location to another location.

The term "after transportation" or "post-transportation period" refers to a period of time in the range of about 0.5 hours to about 72 hours, for instance, about 1 to about 72 hours, about 5 to about 70 hours, about 10 to about 70 hours, about 15 to about 65 hours, about 20 to about 60 hours, about 25 to about 55 hours, about 30 to about 50 hours, or about 35 to about 45 hours, preferably about 12 hours to about 48 hours, for instance, about 16 to about 44 hours, about 20 to about 40 hours, about 24 to about 36 hours, or about 28 to about 32 hours after transporting a livestock animal from one location to another location.

The term "period during transportation" refers to any period of time during transportation of a livestock animal from one location to another location. It is understood that the length of the period will depend on the time it takes to transport a livestock animal from one location to another. For instance, if the total time needed to transport a livestock animal from one location to another is 3 hours, the "a period during transportation" may be 3 hours, or the first hour of transportation or the last hour of transportation, and so on, etc.

In an embodiment, the duration of the feed deprivation period is substantially the same as the duration of the pre-slaughter period or the pre-transport period, i.e., about 0.05 hour to about 72 hours, for instance, about 1 hour to about 72 hours, about 10 to about 70 hours, about 15 to about 65 hours, about 20 to about 60 hours, about 25 to about 55 hours, about 30 to about 50 hours, or about 35 to about 45 hours, preferably about 12 hours to about 48 hours, for instance, about 16 to about 44 hours, about 20 to about 40 hours, about 24 to about 36 hours, or about 28 to about 32 hours. In an embodiment, the duration of the feed deprivation period is substantially the same as the period during transportation, i.e., the total time it takes to transport a livestock animal from one location to another location.

The term "osmolarity" or "osmotic concentration," as used herein, refers to the measure of solute concentration, defined as the number of osmoles (Osm) of solute per liter (L) of solution (osmol/L or Osm/L). The osmolarity of a solution is usually expressed as Osm/L (pronounced "osmolar"), in the same way that the molarity of a solution is expressed as "M" (pronounced "molar"). Whereas molarity measures the number of moles of solute per unit volume of solution, osmolarity measures the number of osmoles of solute particles per unit volume of solution. This value allows the measurement of the osmotic pressure of a solution and the determination of how the solvent will diffuse across a semipermeable membrane (osmosis) separating two solutions of different osmotic concentration. Osmolarity is distinct from molarity because it measures osmoles of solute particles rather than moles of solute. The distinction arises because some compounds can dissociate in solution, whereas others cannot. Ionic compounds, such as salts, can dissociate in solution into their constituent ions, so there is not a one-to-one relationship between the molarity and the osmolarity of a solution. For example, sodium chloride (NaCl) dissociates into Na+ and Cl− ions. Thus, for every 1 mole of NaCl in solution, there are 2 osmoles of solute particles (i.e., a 1 mol/L NaCl solution is a 2 osmol/L NaCl solution). Both sodium and chloride ions affect the osmotic pressure of the solution. Non-ionic compounds do not dissociate, and form only 1 osmole of solute per 1 mole of solute. For example, a 1 mol/L solution of glucose is 1 osmol/L. Multiple compounds may contribute to the osmolarity of a solution. For example, a 3 Osm solution might consist of: 3 moles glucose, or 1.5 moles NaCl, or 1 mole glucose+1 mole NaCl, or 2 moles glucose+0.5 mole NaCl, or any other such combination. The skilled person is well-acquainted with the concept of osmolarity and can easily determine the osmolarity of a composition or solution using conventional formulas, for instance, such as set out below:

$$\text{Osmolarity} = \Sigma v_i c_i$$

where $v_i$ is the number of particles formed by the dissociation of one molecule of the $i^{th}$ solute; and $c_i$ is the molar concentration of the $i^{th}$ solute in solution.

The term "effective solute" or "non-penetrating solute," as used herein, refers to a solute (e.g., NaCl) that can exert an osmotic force across a membrane. In other words, an effective solute is one that cannot cross, for instance, the membrane of a cell and as a result will cause a water movement either inside or outside the cell. Non-limiting examples of effective solutes include sodium ions, potassium ions, chloride ions, magnesium ions.

The term "ineffective solute," as used herein, refers to a solute (e.g., glycerol, glucose), which does not exert an osmotic force across a membrane. In other words, an ineffective solute is one that can cross, for instance, the membrane of a cell and as a result will not cause a water movement either inside or outside the cell. Non-limiting example of ineffective solutes include glycerol, glucose, urea and others.

The term "tonicity," as used herein, refers to a measure of the effective osmotic pressure gradient (as defined by the water potential of the two solutions) of two solutions separated by a semipermeable membrane. In other words, tonicity is the relative concentration of the effective solutes that determine the direction and extent of diffusion. It is commonly used when describing the response of cells immersed in an external solution. Tonicity is influenced only by solutes that cannot cross the membrane (i.e., effective solutes), as only these exert an effective osmotic pressure. Such solutes are referred to as "effective solutes" or "non-penetrating solutes." Solutes able to freely cross the membrane do not affect tonicity because they will always be in equal concentrations on both sides of the membrane. Such solutes are referred to as "ineffective solutes."

In this disclosure, when the composition as taught herein solely contains effective solutes (i.e., solutes not capable of penetrating the membrane, e.g., cell membrane), the tonicity of the solution will parallel its osmolarity relative to the cell such that a hyposmotic solution will also be an hypotonic solution or an isosmotic solution will also be an isotonic or a hyperosmotic solution will also be an hypertonic solution.

In this disclosure, when the composition as taught herein contains a mixture of effective (non-penetrating) and ineffective (penetrating) solutes, tonicity will be influenced solely by the effective solutes present in the composition. In other words, water will move towards the area where the highest concentration of effective (non-penetrating) solutes is, for instance, outside the cells. In this case, the concentration of the ineffective (penetrating) solutes will have no impact on tonicity of the composition. Therefore, in certain embodiments, one or more ineffective solutes may be added to the compositions as taught herein without affecting tonicity, irrespective of their effect on osmolarity (e.g., even if they cause osmolarity to be greater than 300 mosm/L).

The skilled person is well-acquainted with the concept of tonicity and can easily determine the tonicity of a composition or solution. There are three classifications of tonicity that one solution can have relative to a cell, namely: 1) isotonic, 2) hypertonic, and 3) hypotonic.

The term "isotonic composition," as used herein, refers to a composition having a concentration of effective solutes, primarily related to the concentrations of the electrolytes, in an amount that is not significantly different than the concentration of that ingredient found in the physiological fluids of the animal (e.g., livestock animal) such as plasma, interstitial and intracellular fluids. In biology, an isotonic solution is one that has an effective osmole concentration that is the same as the solute concentration of a cell. In this case the cell neither swells nor shrinks because there is no concentration gradient for water across the cell membrane. Water molecules diffuse through the plasma membrane in both directions, and as the rate of water diffusion is the same in each direction that cell will neither gain nor lose water. A non-limiting example of isotonic solution is a physiological saline solution (also know as isotonic saline), i.e., a solution of 0.90% w/v of NaCl, having an osmolarity of 308 mOsm/L.

The term "hypertonic composition," as used herein, refers to a composition having a concentration of effective solutes, primarily related to the concentrations of the electrolytes, in an amount that is greater than the concentration of that ingredient found in the physiological fluids of the animal such as plasma, interstitial and intracellular fluids. In biology, a hypertonic solution is one with a higher concentration of solutes outside the cell than inside the cell. When a cell is immersed into a hypertonic solution, the tendency is for water to flow out of the cell in order to balance the concentration of the solutes. Likewise, the cytosol of the cell is conversely categorized as hypotonic, opposite of the outer solution. A non-limiting example of hypertonic solution would be a saline solution that has more than 0.90% w/v of NaCl and an osmolarity greater than 308 mOsm/L.

The term "hypertonic composition," as used herein, refers to a composition having a concentration of effective solutes, primarily related to the concentrations of the electrolytes, in an amount that is lower than the concentration of that ingredient found in the physiological fluids of the animal such as plasma, interstitial and intracellular fluids. In biology, a hypotonic solution has a lower concentration of solutes outside the cell than inside the cell. In an attempt to balance the concentrations of solutes inside and outside the cell, water will typically go into the cell, and may cause it to burst in extreme cases. A non-limiting example of hypotonic solution would be a saline solution that has less than 0.90% w/v of NaCl and an osmolarity lower than 308 mOsm/L. In an embodiment, a hypotonic composition as taught herein has a minimum concentration of 3 grams of electrolytes per liter of water.

The term "carcass weight" (also known as "dressed weight") refers to the weight of an animal post slaughter, after removing all the internal organs and head, as well as inedible (or less desirable) portions of the tail and legs. In this disclosure, increased carcass weight is also referred to as "increased carcass yield," e.g., more meat is harvested.

The term "alkalinizing agent(s)," as used herein, refers to compounds or substances suitable for restoring the alkalinity (i.e., the amount of alkali or base in a solution, which is often expressed in terms of pH) of a solution or blood. In biology, alkalinizing agents are often used to manage disorders associated with low pH of the blood, e.g., for treating acidosis due to renal failure. Non-limiting examples of alkalinizing agents include anions of, as well as any salts thereof, propionate, bicarbonate (e.g., sodium bicarbonate), citrate (e.g., potassium citrate), carbonate (e.g., calcium carbonate), lactate (e.g., sodium lactate), acetate (e.g., calcium acetate), and others. Propionate and sodium bicarbonate are non-limiting examples of commonly preferred alkalinizing agents.

The term "gluconeogenic precursor(s)," as used herein, refers to compounds or substances involved in the gluconeogenesis metabolic pathway that results in the generation of glucose in a living organism. Non-limiting examples of gluconeogenic precursor(s), include glycerol, propylene glycol, dextrose, lactate, propionate, glucogenic amino acids such as alanine, glutamine, glycine, serine, valine, histidine, arginine, cysteine, proline, glutamate, aspartate, asparagine, methionine, phenylalanine, isoleucine, threonine, tyrosine or tryptophan, and sugars (e.g., sucrose, maltose). In this disclosure, one or more gluconeogenic precursors may be added to the compositions as taught herein for the purpose of providing a livestock animal with a source of energy to help sustain metabolic functions and/or spare muscle glycogen, for instance, during a period of feed deprivation such as during the pre-slaughter period. In a suitable embodiment, the gluconeogenic precursor is an ineffective solute.

The term "live body weight or mass" (usually expressed in kg), as used herein, refers to the body weight or mass of a livestock animal while still alive, e.g., just before slaughter or during a period surrounding transportation from one location to another location (e.g., before, during and/or after transportation). In this disclosure, the live body weight of a livestock animal is the body weight before slaughter or during a period surrounding transportation from one location to another location (e.g., before or after transportation or at any time during the transportation period), e.g., about 0.05 hour to about 72 hours, for instance, about 1.0 hour to about 72 hours, for instance, about 10 to about 70 hours, about 15 to about 65 hours, about 20 to about 60 hours, about 25 to about 55 hours, about 30 to about 50 hours, or about 35 to about 45 hours, preferably about 12 hours to about 48 hours, for instance, about 16 to about 44 hours, about 20 to about 40 hours, about 24 to about 36 hours, or about 28 to about 32 hours before slaughter or during a period surrounding transportation from one location to another location (e.g., before or after transportation or at any time during the transportation period). Typically, a feed deprivation-induced decrease in live body weight in a livestock animal translates into or correlates with a decrease in carcass weight or carcass yield after slaughter of the livestock animal and/or deterioration of the well-being or health of the livestock animal (e.g., deterioration of the physiological condition in terms of body weight, muscle mass, fur, wool, hair, skin, appetite, reflexes, digestion, etc.) and/or medical or health state (e.g., presence or absence of diseases or infections etc.) after a period of transportation from one location to another location.

The term "well-being" or "health" of a livestock animal as used herein refers to a general term for the condition of an animal (e.g., livestock animal) in terms of its social (e.g., social behavior), psychological (e.g., mental alertness), physiological (e.g., body weight, muscle mass, fur, wool, hair, skin, appetite, reflexes, digestion, etc.) and/or medical or health state (e.g., presence or absence of diseases or infections etc.).

The term "about," as used herein, indicates a range of normal tolerance in the art, for example, within 2 standard deviations of the mean. The term "about" can be understood as encompassing values that deviate at most 10%, 9%, 8%, 7%, 6%, 5%, 4%, 3%, 2%, 1%, 0.5%, 0.1%, 0.05%, or 0.01% of the indicated value.

The terms "comprising" or "to comprise" and their conjugations, as used herein, refer to a situation wherein the terms are used in their non-limiting sense to mean that items following the word are included, but items not specifically mentioned are not excluded. It also encompasses the more limiting verbs "to consist essentially of" and "to consist of."

Reference to an element by the indefinite article "a" or "an" does not exclude the possibility that more than one of the elements is present, unless the context clearly requires that there be one and only one of the elements. The indefinite article "a" or "an" thus usually means "at least one."

The term "test livestock animal," as used herein, refers to a livestock animal (e.g., beef, poultry such as broiler chickens) administered with compositions as taught herein. The term "control livestock animal" refers to a livestock animal (e.g., beef, poultry such as broiler chickens) not administered with a composition as taught herein or administered with water or a composition wherein the potassium to sodium ratio is lower than one. In an embodiment of this disclosure, the control livestock animal is a livestock animal (e.g., beef or poultry such as broiler chicken) not administered with any composition or administered with water or a composition wherein the potassium to sodium ratio is lower than one, preferably of the same genus and/or species as the test livestock animal (e.g., beef or poultry such as broiler chickens).

In this disclosure, the terms "to minimize" and "minimized live body weight loss" or "minimized carcass weight loss" or "minimized carcass yield loss" of a livestock animal (e.g., beef, poultry such as broiler chickens), as used herein refer to the ability to significantly minimize or to have significantly minimized live body weight loss or carcass weight loss or carcass yield loss of a test livestock animal compared to the live body weight loss or carcass weight loss or carcass yield loss of a control livestock animal. Generally, the live body weight loss or carcass weight loss or carcass yield loss of a test livestock animal is minimized when it is at least 5%, such as at least 10%, 15%, 25%, 30%, 35%, 40%, 45%, or 50% less than the corresponding live body weight loss or carcass weight loss or carcass yield loss of a control livestock animal. For example, a livestock animal subjected to a prolonged feed deprivation, for instance, during the pre-slaughter period or during a period surrounding transportation (e.g., before, during or after transportation), loses about 5% of its live body weight, whereas a test livestock animal treated with the composition as taught herein loses less live body weight, e.g., only 3% of its live body weight loss, resulting in 40% less live body weight loss than would normally occur.

Carcass weight or carcass yield may be considered increased when the carcass weight or yield of a test livestock animal (i.e., administered with the composition as taught herein it is at least 0.5%, such as at least 1%, 1.5%, 2%, 2.5%, 3%, 3.5%, 4.0%, 4.5%, 5%, 6%, 7%, 8%, 9%, or 10% or more, higher than the corresponding carcass weight or carcass yield of a control livestock animal.

Alternatively or additionally, the live body weight loss or carcass weight loss or carcass yield loss of a test livestock animal may be increased or decreased when it is statistically significantly minimized compared to the live body weight loss or carcass weight loss or carcass yield loss of a control livestock animal.

The term "meat quality deterioration," as used herein, refers to a deterioration in meat quality. The perception of meat's juiciness or dryness depends on the binding of water to muscle proteins, and this process is influenced by pH. Water-holding capacity is best in meat with a pH of around 5.8. A pH that is too low or too high results in less than desirable meat. After slaughter, when muscle turns into meat, glycogen is broken down to lactic acid, which causes the pH to decrease. In general, prolonged feed deprivation such as during the pre-slaughter period or during a period surrounding transportation from one location to another location (e.g., before, during and/or after) affects meat quality, for instance, taste, color, juiciness, tenderness, dryness, and the like, thereby making the meat less attractive to consumers. When meat quality deterioration is minimized, it means that the meat quality is perceived to be of higher quality by consumers. In contrast, meat quality may be considered improved when the meat is perceived to be of higher quality by consumers.

In this disclosure, the term "to prevent or minimize live body weight loss or carcass weight loss or carcass yield loss during the pre-slaughter period or during periods surrounding transportation from one location to another location (e.g., before, during and/or after transportation)," as used herein, refers to substantially no changes in live body weight loss or carcass weight loss or carcass yield loss during the pre-slaughter period or during periods surrounding transportation from one location to another location (e.g., before, during and/or after transportation).

In this disclosure, the term "preventing or minimizing feed deprivation-induced effects on the well-being or health of a livestock animal during periods surrounding transportation of the livestock animal from one location to another location (e.g., before, during and/or after transportation)" as used herein refers to substantially no changes in the well-being or health of the livestock animal during periods surrounding transportation from one location to another location (e.g., before, during and/or after transportation), (e.g., no substantial change in the physiological condition of the livestock animal in terms of body weight, muscle mass, fur, wool, hair, skin, appetite, reflexes, digestion, etc.) and/or its medical or health state (e.g., presence or absence of diseases or infections etc.).

DETAILED DESCRIPTION

Figure 1:
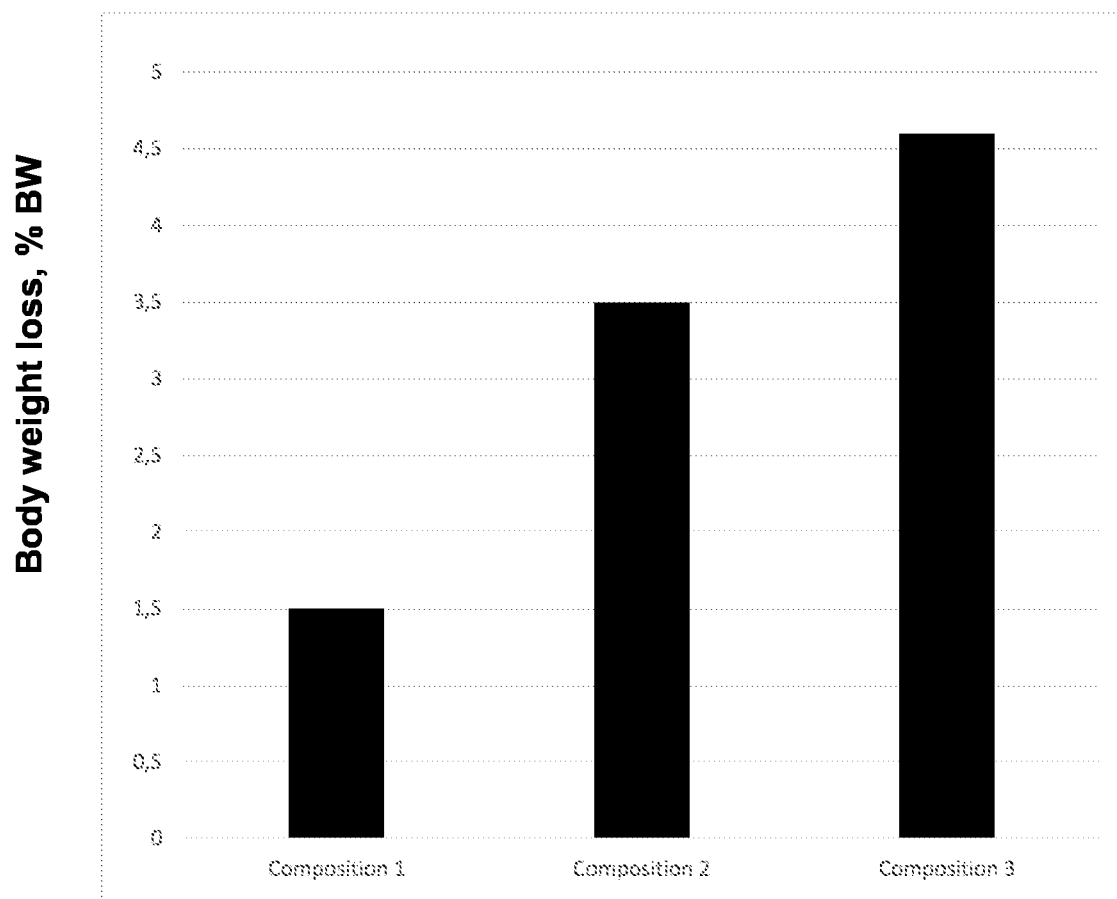
FIG. 1: Effect of aqueous compositions with varying potassium to sodium ratio on the live body weight of Holstein bulls subjected to a 24-hour feed deprivation period.

Existing electrolyte-based feed supplement compositions for livestock animals are characterized in that they are more concentrated in sodium than potassium, i.e., wherein the ratio of sodium to potassium is greater than one (e.g., selectrolyte, solulyte concentrate, glucotrans, and others).

The present inventors surprisingly found that an electrolyte-based liquid composition, which is more concentrated in potassium than sodium (i.e., wherein the molar ratio of potassium to sodium is greater than one), and which is (as a whole) isotonic or hypotonic, can efficiently prevent or minimize live body weight loss in livestock animals (e.g., beefs, poultry such as broiler chickens, etc.) during a period of prolonged feed deprivation (e.g., such as during the pre-slaughter period or during period surrounding transportation from one location to another location (e.g., before, during and/or after transportation) in contrast to traditional electrolyte-based compositions (i.e., wherein the sodium to potassium molar ratio is greater than one). It was further found that administering a livestock animal (e.g., beefs, poultry such as broiler chickens, etc.) with a composition according to the disclosure, prior to slaughter, leads to increased carcass weight or carcass yield as well as improved meat quality compared to what is achieved with traditional compositions. It was also found that administering a livestock animal (e.g., beefs, poultry such as broiler chickens, etc.) with a composition according to the disclosure during a period surrounding transportation from one location to another location (e.g., before, during or after transportation), leads to improved well-being or health of livestock animal during periods surrounding transportation from one location to another location (e.g., before, during and/or after transportation) compared to what is achieved with traditional compositions.

Without wishing to be bound to any theories, it is believed that the compositions of this disclosure are particularly well-suited for situations involving a prolonged period of feed deprivation, such as during the pre-slaughter period or during periods surrounding transportation from one location to another location (e.g., before, during or after transportation). During the pre-slaughter period or periods surrounding transportation from one location to another location (e.g., before, during or after transportation), livestock animals are often held in an environment without feed for a prolonged period, e.g., from about 0.05 hours to 72 hours or about 5 hours to about 72 hours. This causes the livestock animals to loose or excrete potassium via the kidneys at a greater rate than sodium. This in turn causes a disruption of the osmotic balance between the intracellular and extracellular milieu, driving water out of the cells, ultimately leading to live body weight loss, carcass weight or yield loss and/or poor meat quality as well as deterioration of the well-being or health of the livestock animal. It was surprisingly found that live body weight loss, carcass weight loss and/or meat quality deterioration as well as deterioration of the well-being or health of the livestock animal could be prevented or minimized by administering the composition of this disclosure to a livestock animal prior to slaughter (e.g., about 0.05 hours to about 72 hours, for instance, about 5 hours to about 72 hours before slaughter) or during a period surrounding transportation (e.g., about 0.05 hours to about 72 hours before transportation; or, e.g., about 5 hours to about 72 hours after transportation; or, e.g., during transportation such as at any time point during the transportation period).

Aqueous Compositions

In a first aspect, an aqueous composition for a livestock animal comprising potassium and sodium is disclosed, wherein the potassium to sodium ratio is greater than one, such as, for instance, a ratio of 55:45, 60:40, 65:35, 70:30, 75:25, 80:20, 85:15, 90:10 or 95:05, and wherein the composition is hypotonic or isotonic.

In this disclosure, the composition as taught herein is considered "hypotonic" when its osmolarity is greater than about 100 mosm/L and lower than about 320 mosm/L, e.g., between about 100 and about 300 mosm/L or between about 105 and about 295 mosm/L or between about 110 and about 290 mosm/L or between about 120 and about 280 mosm/L or between about 130 and about 270 mosm/L or between about 140 and about 260 mosm/L or between about 150 and about 250 mosm/L or between about 160 and about 240 mosm/L or between about 170 and about 230 mosm/L or between about 180 and about 220 mosm/L or about 190 and about 210 mosm/L.

In this disclosure, the composition as taught herein is considered "isotonic" when its osmolarity is about around 300 mosm/L.

In an embodiment, the potassium to sodium ratio is in the range of about 65:35 to about 95:05, such as 65:35, 70:30, 75:25, 80:20, 85:15, 90:10 or 95:05, preferably at least 75:25. The present inventors found that when a livestock animal (e.g., a beef or a poultry such as a broiler chicken) is administered with the composition as taught herein (i.e., having a potassium to sodium ratio is greater than one), the negative impact of prolonged feed deprivation (e.g., during the pre-slaughter period or during a period surrounding transportation (e.g., before, during or after transportation) on live body weight loss was minimized or prevented or counteracted in the livestock animal compared to a livestock animal not administered with the composition of this disclosure or that is administered with a composition wherein the potassium to sodium ratio is lower than one. It was also found that the carcass weight loss or carcass yield loss as well as meat quality deterioration associated with prolonged feed deprivation (e.g., during the pre-slaughter period) was minimized or prevented or counteracted in the livestock animal compared to a livestock animal not administered with the composition of this disclosure or that is administered with a composition wherein the potassium to sodium ratio is lower than one. It was also found that the deterioration of the well-being or health associated with prolonged feed deprivation (e.g., during the pre-slaughter period) was minimized or prevented or counteracted in the livestock animal compared to a livestock animal not administered with the composition of this disclosure or that is administered with a composition wherein the potassium to sodium ratio is lower than one.

It was found that the effects of the compositions as taught herein on feed deprivation-induced live body weight loss, carcass weight loss and/or carcass yield loss, meat quality deterioration, as well as deterioration of the well-being or health of a livestock animal were further enhanced when the potassium to sodium ratio was in the range of about 65:35 to about 95:05, such as 65:35, 70:30, 75:25, 80:20, 85:15, 90:10 or 95:05. Particularly good results (i.e., minimized carcass weight loss or yield, improved meat quality, as well as improved well-being or health) were observed when the potassium to sodium ratio was in the range of at least 75:25.

It was further observed that when the composition as taught herein (i.e., having the potassium to sodium ratio as described above) is in an isotonic state (i.e., a composition, which as a whole, will not cause any significant water movement inside or outside the cells of an organism), its effects on feed deprivation-induced live body weight loss, carcass weight loss and/or carcass yield loss, minimized meat quality deterioration as well as well deterioration of the well-being or health of a livestock animal were further enhanced. Therefore, the compositions as taught herein, when in an isotonic state, may be particularly advantageous to prevent or reduce the severity or occurrence of feed deprivation-induced live body weight loss and/or carcass weight or yield loss, poor meat quality as well as deterioration of the well-being or health of a livestock animal (e.g., beef, poultry such as broiler chickens) during a period of prolonged feed deprivation, such as, for instance, during the pre-slaughter period or during periods surrounding transport (e.g., before, during or after) to the slaughter house or to other locations or other instances involving prolonged feed deprivation.

It was further observed that when the composition as taught herein (i.e., having the potassium to sodium ratio as described above) is in an hypotonic state (i.e., a composition, which as a whole, will cause water to go inside the cells of an organism, e.g., beef), its effects on feed deprivation-induced carcass weight loss or carcass yield loss, poor meat quality, as well as deterioration of the well-being or health of a livestock animal were further enhanced. Therefore, the compositions of the disclosure, when in an hypotonic state, may be particularly advantageous to prevent or reduce the severity or occurrence of feed deprivation-induced live body weight loss and/or carcass weight or yield loss, poor meat quality as well as deterioration of the well-being or health of a livestock animal during a period of prolonged feed deprivation, such as, for instance, during the pre-slaughter period or during periods surrounding transport (e.g., before, during and/or after) to the slaughter house or other locations other instances involving prolonged feed deprivation.

In an embodiment, the composition as taught herein (i.e., having a potassium to sodium ratio greater than one and that is, as a whole, isotonic or hypotonic) may further comprise one or more electrolytes selected from magnesium, calcium, chloride, bicarbonate or carbonate, acetate, propionate, sulphate and phosphate.

In a preferred embodiment, the composition as taught herein comprises at least magnesium. It was surprisingly observed that adding magnesium to the compositions as taught herein improved the efficacy of the compositions as taught herein, i.e., better prevented loss in live body weight and/or loss in carcass weight or yield as well as deterioration of the well-being or health or reduced or minimized the loss in live body weight and/or carcass weight or yield as well as deterioration of the well-being or health of a livestock animal, as would normally occur in response to a prolonged period of feed deprivation.

In a further preferred embodiment, the composition as taught herein may further comprise ions of magnesium, chloride, carbonate or bicarbonate, and/or acetate.

In an embodiment, the total amount of effective electrolytes (i.e., non-penetrating or effective solutes) that is present in the composition as taught herein (i.e., having a potassium to sodium ratio greater than one and that is, as a whole, isotonic or hypotonic) has an osmolarity in the range of about 100 to about 320, 310, or 300 mosm/L, such as, for instance, 125 to 275 mosm/L, 150 to 250 mosm/L, or 175 to 225 mosm/L. For example, when the composition as taught herein comprises a potassium salt and a sodium salt as the sole electrolytes, the osmolarity of the total electrolytes (i.e., potassium salt and sodium salt) is in the range of about 100 to about 300 mosm/L, such as, for instance, 125 to 275 mosm/L, 150 to 250 mosm/L, or 175 to 225 mosm/L. In a further example, when the composition as taught herein comprises potassium salt, sodium salt and magnesium salt as the sole electrolytes, the osmolarity of the total electrolytes (i.e., potassium salt, sodium salt and magnesium salt) is in the range of about 100 to about 300 mosm/L, such as, for instance, 125 to 275 mosm/L, 150 to 250 mosm/L, or 175 to 225 mosm/L., and so on. Therefore, it is understood that it is the total amount of electrolytes (e.g., potassium, sodium, magnesium) present in the composition of the disclosure that has an osmolarity in the range of about 100 to about 300 mosm/L, such as, for instance, 125 to 275 mosm/L, 150 to 250 mosm/L, or 175 to 225 mosm/L, and not the composition as a whole.

In an embodiment, the composition as taught herein may have an osmolarity that exceeds 300 mosm/L when comprising an additional compound that is an ineffective solute (penetrating solute). One example of such ineffective solute is glycerol. Glycerol contributes to the osmolarity of the composition, but does not have any effect on the tonicity of the composition taught herein. For instance, the composition as taught herein may comprise a concentration of electrolytes such as potassium salts and sodium salts, which are effective solutes having a total osmolarity of about 300 mosm/L, and may further comprise an ineffective solute such as glycerol. Despite increasing the osmolarity beyond 300 mosm/L, such composition would still be isotonic.

In an embodiment, when the composition as taught herein comprises effective solutes only, the osmolarity may not exceed 320, 310, or 300 mosm/L. For instance, the composition as taught herein may comprise a concentration of effective solutes such as potassium salts and sodium salts having a total osmolarity of about 150 mosm/L and may further comprise another effective solute, such as magnesium salts, having an osmolarity of 150 mosm/L. In this case, the osmolarity of the composition as a whole does not exceed 300 mosm/L.

In an embodiment, the composition as taught herein further comprises one or more gluconeogenic precursor. It was found that it may be advantageous to add one or more gluconeogenic precursors to the composition as taught herein to provide a source of energy to the livestock animal during a period of feed deprivation, such as during the pre-slaughter period or periods surrounding transportation from one location to another (e.g., before, during and/or after). Specifically, it was found that adding one or more gluconeogenic precursors in the composition as taught herein better prevented or minimized live body weight loss, and/or carcass weight loss or carcass yield loss, meat quality deterioration as well as deterioration of the well-being or health associated with prolonged period of feed deprivation. Any suitable gluconeogenic precursor may be added to the compositions of this disclosure.

In an embodiment, the one or more gluconeogenic precursors are selected from glycerol, propylene glycol, dextrose, lactate, amino acid, and sugar, and others.

In an embodiment, the amino acid may be any glucogenic amino acid. In a preferred embodiment, the amino acid is selected from alanine and glutamine.

In an embodiment, the sugar may be any sugars, such as sucrose, maltose, glucose or dextrose, fructose, galactose, lactose and the like. In a preferred embodiment, the sugar is selected from sucrose and maltose.

In a preferred embodiment, the one or more gluconeogenic precursors does not affect the tonicity of the composition as taught herein, i.e., the composition remains isotonic or hypotonic, i.e., such gluconeogenic precursors are ineffective solutes. Non-limiting example of such gluconeogenic precursor include glycerol and propylene glycol. It will be appreciated that when adding a gluconeogenic precursor such as glycerol, the tonicity of the composition as taught herein will not be changed or affected despite a change in osmolarity.

In an embodiment, the one or more gluconeogenic precursors may affect the tonicity of the composition as taught herein, i.e., they are effective solutes. The addition of such compound into the composition as taught herein would contribute to or affect the tonicity of the composition.

In a preferred embodiment, the gluconeogenic precursor may be glycerol. It was found that adding glycerol to the compositions of the disclosure may be particularly advantageous because it further improved the efficacy of the compositions in terms of preventing and/or minimizing feed deprivation-induced live body weight loss and/or carcass weight loss or carcass yield loss, quality deterioration (i.e., meat quality was improved) as well as deterioration of the well-being or health of livestock animals prior to slaughter or during periods surrounding transportation from one location to another location (e.g., before, during and/or after).

In an embodiment, the composition as taught herein may further comprise one or more alkalinizing agents. It was found that it may be advantageous to add one or more alkalinizing agents to the composition as taught herein to prevent disturbances or help normalize blood pH in livestock animal subjected to prolonged feed deprivation, such as during the pre-slaughter period or during periods surrounding transportation (e.g., before, during and/or after). Prolonged feed deprivation in animals (e.g., livestock animals) may lead to a condition referred to "acidosis," which is an increased acidity in the blood and other body tissue (i.e., an increased hydrogen ion concentration). Acidosis typically occurs when arterial pH falls below 7.35, while its counterpart (alkalosis) occurs at a pH over 7.45. Any suitable alkalinizing agents may be added to the composition of this disclosure, i.e., compounds capable of preventing changes in pH (i.e., going below pH<7.35) or capable of restoring pH to physiological levels (i.e., around pH 7.4) or capable of reversing acidosis.

In an embodiment, the one or more alkalinizing agents may be selected from propionate, bicarbonate, citrate, carbonate, lactate and acetate anions or any salts thereof.

In a preferred embodiment, the alkalinizing agent is a propionate anion or any salt therefore and/or acetate. It may be advantageous to add propionate and acetate to the compositions as taught herein to facilitate sodium and water absorption in the small intestine as well as produce energy when metabolized.

In an embodiment the livestock animal may be any livestock animals, for instance, any domesticated animals raised in an agricultural setting for commercial purposes (e.g., meat, wool, milk, etc.), such as cattle (e.g., beef), sheep, goats, swine, poultry (including egg-producing poultry and broiler chickens), and equine animals. In an embodiment, the livestock animal may be any ruminants or any monogastric animals.

In an embodiment, the livestock animal may be a ruminant selected from bovine, ovine and caprine. Non-limiting examples of bovine include bulls (beef), steers, stags, heifers, cows, calves, oxen, and the like. Non-limiting examples of ovine include sheep, mouflon, urial, and the like. Non-limiting examples of caprine include goat, ibex, markhor and the like.

In this disclosure, bovine, ovine and caprine animals include both domestic and wild bovine, ovine and caprine animals and male and female bovine, ovine and caprine animals (particularly male bovine, ovine and caprine animals).

In a preferred embodiment, the livestock animal is a growing bovine, (e.g., steer, heifer or bull destined for meat production.

In an embodiment, the livestock animal may be a monogastric animal selected from poultry (e.g., broiler chickens), swine (e.g., pigs), or horses. In a preferred embodiment, the livestock animal is poultry, (e.g., broiler chickens, which are chickens reared and prepared for meat consumption for the broiler industry.

In a further aspect, a concentrate suitable for the preparation of the composition as taught hereinabove is disclosed that, when diluted in water, provides a composition as taught hereinabove, i.e., having a potassium to sodium ratio that is greater than one and that is (as a whole) isotonic or hypotonic. In an embodiment, the concentrate is about 5 to 50 times, for instance, 8 to 45 times, 10 to 40 times, 12 to 35 times, 15 to 30 times, 17 to 25 times, 18 to 20 times, more concentrated than the composition as taught hereinabove.

In this disclosure, the concentrate composition may be reconstituted at the time of use (e.g., just before administering to a livestock animal) by the addition of a solvent (e.g., water) in a suitable amount so that the resulting composition has the properties as taught herein. Therefore, it is understood that when the compositions as taught herein are in the form of "concentrates" or "concentrate compositions," the compositions are not immediately suitable for administration to a livestock animal because they must be first reconstituted in a suitable amount of liquid (e.g., water) so as to achieve the characteristics as taught herein, i.e., having a potassium to sodium ratio that is greater than one and that is (as a whole) isotonic or hypotonic.

It is also understood that the term "concentrate" or "concentrate composition" also encompasses instances where the ingredients (e.g., salts and/or others) of the compositions as taught herein are present in an amount that is about 5- to about 50-fold more elevated, for instance, 8- to 45-fold, 10- to 40-fold, 12- to 35-fold, 15- to 30-fold, 17- to 25-fold, 18- to 20-fold, preferably about 20-fold more elevated than the same ingredients (e.g., salts and/or others) present in a composition ready for use, i.e., composition having the properties as taught herein. It is thus understood that such concentrate (e.g., in a dry form or liquid form or gel form) can be diluted in water by a factor of about 5 to about 50, for instance, 8 to 45, 10 to 40, 12 to 35, 15 to 30, 17 to 25, 18 to 20, preferably about 20, so as to obtain an composition as taught herein, i.e., having a potassium to sodium ratio that is greater than one and that is (as a whole) isotonic or hypotonic, and, thus, that is ready for use, i.e., ready to be administered to, or ready to be ingested by, a livestock animal.

In an embodiment, the composition or concentrate as taught herein may be in a dry form (e.g., dry powder, crystals) or gel form or liquid form, preferably liquid form, for instance, aqueous form.

The skilled person knows how to make the compositions as taught herein, as well as concentrates as taught herein, that have the properties as taught herein, i.e., having a potassium to sodium ratio that is greater than one and that is (as a whole) isotonic or hypotonic. For instance, the skilled person knows how to dissolve suitable amounts of electrolytes, e.g., in the form of salts, and optionally any other additional compounds (e.g., gluconeogenic precursor like glycerol and/or alkalinizing agent such as propionate anions or salt thereof, in drinking water so as to arrive at the compositions of this disclosure. For instance, a non-limiting example of a composition having a potassium to sodium molar ratio of 75:25 can be prepared by adding the following ingredients to one liter of drinking water:

| Salt | g/Kg product | g/L drinking water |
| --- | --- | --- |
| NaCl | 36.27 | 0.276 |
| Na propionate | 155.4 | 1.181 |
| KCl | 497.4 | 3.78 |
| MgAc | 310.9 | 2.36 |

This results in a composition having the following characteristics: 3.63% NaCl; 15.54% Na propionate; 49.74% KCl; 31.09 MgAcetate (MgAc). The mixture obtained has an osmolarity of 200 mosm/L (provided by the total amount of electrolytes present in the mixture) and is hypotonic.

Methods of the Disclosure

In a further aspect, a method for preventing or minimizing live body weight loss in livestock animals subjected to feed deprivation is disclosed, comprising the step of:
administering to the livestock animal an effective amount of the composition as taught herein at the onset of and/or during and/or after a period of feed deprivation and/or after the period of feed deprivation has been ended.

In a further aspect, a method for minimizing carcass weight loss or carcass yield loss and/or meat quality deterioration is disclosed, comprising the step of:
administering a livestock animal with an effective amount of the composition as taught herein within a period of about 0.05 hour to about 72 hours or about 5 hours to 72 hours, preferably 12 to about 48 hours prior to slaughter; or within a period of about 0.05 to about 72 hours, preferably about 1 to about 48 hours prior to transportation from one location to another location; or within a period of about 0.05 to about 72 hours, preferably about 1 to about 48 hours after transportation from one location to another location.

In a further aspect, a method for preventing or minimizing deterioration of the well-being or health of a livestock animal is disclosed, comprising the step of:
administering to the livestock animal an effective amount of the composition as taught herein within a period surrounding transportation of the livestock animal from one location to another location, (e.g., within a period before transportation such as within about 0.05 to about 72 hours, preferably about 1 to about 48 hours or about 1 to about 24 hours prior transportation; or, e.g., within a period after transportation such as within about 0.05 to about 72 hours, preferably about 1 to about 48 hours or about 1 to about 24 hours after transportation; or within a period during transportation, e.g., at any time(s) during transportation such as within about 1 minute from the onset of transportation, about 15 minutes from the onset of transportation, about 30 minutes from the onset of transportation, about 45 minutes from the onset of transportation, about 1 hour from the onset of transportation, about 2 hours from the onset of transportation, and so on. It is understood that the timing for administering the composition as taught herein during transportation will depend on the total duration of the transportation period. In an embodiment, the composition as taught herein may also be provided during the entire duration of the transportation period, e.g., ad libitum. For instance, if the total duration of the transportation period from one location to another location is 3 hours, then the composition as taught herein may be administered or made available to the livestock animal for 3 hours, e.g., ad libitum during the whole 3 hour-period.

In the methods as taught above, the step of administering the composition as taught herein may be performed by any suitable manner. For instance, the composition as taught herein may be provided or diluted in the drinking water, and thus may be voluntary ingested or swallowed by the livestock animal (e.g., beef or poultry such as broiler chickens).

In an embodiment, the composition as taught herein may be provided or administered as a drench, where a suitable amount of liquid composition as taught herein is administered to the livestock animal by pouring it down the throat.

In an embodiment, the composition as taught herein may be provided or administered via an injection, e.g., intravenous or subcutaneous, of a suitable amount of liquid composition as taught herein.

In an embodiment, an effective amount of composition is an amount that is sufficient to prevent or minimize feed deprivation-induced live body weight loss and/or carcass weight loss or carcass yield loss, meat quality deterioration and/or deterioration of the well-being or health of a livestock animal, or that is sufficient to increase carcass weight or carcass yield and/or to improve meat quality and/or to improve the well-being or health of a test livestock animal administered with such composition and subjected to a prolonged feed deprivation period compared to a control livestock animal subjected to prolonged feed deprivation period and not administered with any compositions or administered with a composition not as taught herein.

In an embodiment, the period of feed deprivation is about 0.05 hour to about 72 hours or 5 hours to 72 hours or about 1 hour to about 48 hours, such as, e.g., about 5 to about 72 hours or about 12 hours to about 48 hours.

In an embodiment, the compositions as taught herein may be provided or administered to the livestock animals according to the methods as taught above, within a period such as about 0.05 hour to about 72 hours, about 5 hours to about 70 hours, about 6 hours to about 68 hours, about 7 hours to about 66 hours, about 8 hours to about 64 hours, about 9 hours to about 62 hours, about 10 hours to about 60 hours, about 11 hours to about 58 hours, about 12 hours to about 56 hours, about 13 hours to about 54 hours, about 14 hours to about 52 hours, about 15 hours to about 50 hours, about 16 hours to about 48 hours, about 17 hours to about 46 hours, about 18 hours to about 44 hours, about 19 hours to about 42 hours, about 20 hours to about 40 hours, about 21 hours to about 38 hours, about 22 hours to about 36 hours, about 23 hours to about 32 hours, about 24 hours to about 30 hours, about 24 hours to about 28 hours, or about 24 hours to about 26 hours from the onset of feed deprivation.

In an embodiment, the compositions as taught herein may be provided or administered to the livestock animals according to the methods as taught above, within a period such as about 0.05 hour to 72 hours, about 5 hours to about 70 hours, about 6 hours to about 68 hours, about 7 hours to about 66 hours, about 8 hours to about 64 hours, about 9 hours to about 62 hours, about 10 hours to about 60 hours, about 11 hours to about 58 hours, about 12 hours to about 56 hours, about 13 hours to about 54 hours, about 14 hours to about 52 hours, about 15 hours to about 50 hours, about 16 hours to about 48 hours, about 17 hours to about 46 hours, about 18 hours to about 44 hours, about 19 hours to about 42 hours, about 20 hours to about 40 hours, about 21 hours to about 38 hours, about 22 hours to about 36 hours, about 23 hours to about 32 hours, about 24 hours to about 30 hours, about 24 hours to about 28 hours, or about 24 hours to about 26 hours after the feed deprivation period has been ended.

In an embodiment, the period of feed deprivation occurs prior to slaughter, for instance, during transport to the slaughter house and/or at the slaughter house. In an embodiment, the compositions as taught herein may be provided at least within 5 hours, preferably at least within 10, 12, 16, 20 hours, more preferably within at least 24 hours prior to slaughter.

In an embodiment, the period of feed deprivation occurs prior the transportation of a livestock animal from one location to another. In an embodiment, the compositions as taught herein may be provided at least within 0.05 hours, such as at least within 1, 2, 4, 6, 8, 10, 12, 16, 20, 24, 30, 40, 50, 60, 70 or 72 hours, more preferably within at least 24 hours prior to being transported from one location to another location.

In an embodiment, the period of feed deprivation occurs during transportation from one location to another, preferably during the entire transportation period. For instance, if the total duration of the transportation period is 10 hours, then the total duration of the feed deprivation period will be 10 hours. In an embodiment, the compositions as taught herein may be provided at any time(s) during transportation period such as within about 1 minute from the onset of transportation, about 15 minutes from the onset of transportation, about 30 minutes from the onset of transportation, about 45 minutes from the onset of transportation, about 1 hour from the onset of transportation, about 2 hours from the onset of transportation, and so on. It is understood that the timing for administering the composition as taught herein during transportation will depend on the total duration of the transportation period. In an embodiment, the composition as taught herein may also be provided during the entire duration of the transportation period (which is substantially the same as the feed deprivation period), e.g., composition may be provided ad libitum during the period. For instance, if the total duration of the transportation period from one location to another location is 10 hours, then the composition as taught herein may be administered or made available to the livestock animal for 10 hours, e.g., ad libitum during the whole 10 hour-period where the livestock animal is free to voluntary ingest or drink the composition as taught herein as many times as desired, during this period.

In an embodiment, the compositions as taught herein may be provided within a reasonable period after the onset of feed deprivation, such as, for instance, within 0.05 hours, such as within 1, 2, 4, 6, 8, 10, 12, 16, 20, 24, 30, 40, 50, 60, 70 or 72 hours, more preferably within 24 hours after the onset of feed deprivation.

In an embodiment, the compositions as taught herein may be provided within a reasonable period after the feed deprivation has ended, such as, for instance, within 0.05 hours, such as within 1, 2, 4, 6, 8, 10, 12, 16, 20, 24, 30, 40, 50, 60, 70 or 72 hours, more preferably within 24 hours after the feed deprivation period has ended.

In an embodiment, the compositions as taught herein may be provided to a livestock animal once (only one time) or more than once (e.g., 2, 3, 4, or 5 times or more) just before (e.g., one hour) or at the onset of feed deprivation, for instance, during the pre-slaughter period, e.g., 5 to 72 hours, for instance, 10 to 70 hours, 15 to 65 hours, 20 to 60 hours, 25 to 55 hours, 30 to 50 hours, or 35 to 45 hours, preferably about 12 hours to 48 hours, for instance, 16 to 44 hours, 20 to 40 hours, 24 to 36 hours, or 28 to 32 hours, before slaughter or, e.g., during a period before transportation such as 0.05 to 72 hours, 5 to 70 hours, 6 to 68 hours, 7 to 66 hours, 8 to 64 hours, 9 to 62 hours, 10 to 60 hours, 11 to 58 hours, 12 to 56 hours, 13 to 54 hours, 14 to 52 hours, 15 to 50 hours, 16 to 48 hours, 17 to 46 hours, 18 to 44 hours, 19 to 42 hours, 20 to 40 hours, 21 to 38 hours, 22 to 36 hours, 23 to 32 hours, 24 to 30 hours, 24 to 28 hours, or 24 to 26 hours before transportation from one location to another location In an embodiment, the compositions as taught herein may be provided to a livestock animal once (only one time) or more than once (e.g., 2, 3, 4, or 5 times or more) just after (e.g., one hour) the feed deprivation period has been ended, for instance, after transportation from one location to another location, such as within about 0.05 hour to about 72 hours, about 1 hour to about 70 hours, about 5 hours to about 70 hours, about 6 hours to about 68 hours, about 7 hours to about 66 hours, about 8 hours to about 64 hours, about 9 hours to about 62 hours, about 10 hours to about 60 hours, about 11 hours to about 58 hours, about 12 hours to about 56 hours, about 13 hours to about 54 hours, about 14 hours to about 52 hours, about 15 hours to about 50 hours, about 16 hours to about 48 hours, about 17 hours to about 46 hours, about 18 hours to about 44 hours, about 19 hours to about 42 hours, about 20 hours to about 40 hours, about 21 hours to about 38 hours, about 22 hours to about 36 hours, about 23 hours to about 32 hours, about 24 hours to about 30 hours, about 24 hours to about 28 hours, or about 24 hours to about 26 hours after transportation from one location to another location (i.e., once arrived at the new location).

In an embodiment, the compositions as taught herein may be provided to a livestock animal once (only one time) or more than once (e.g., 2, 3, 4, or 5 times or more) during the period of feed deprivation, for instance, during the pre-slaughter period (e.g., may include transport to the slaughter house and/or stay at the slaughter house) or during transportation from one location to another location (e.g., which does not necessarily involve slaughtering the livestock animal once it has arrived at the new location).

In an embodiment, the compositions as taught herein may be provided to a livestock animal once (only one time) or more than once (e.g., 2, 3, 4, or 5 times or more) before or at the onset of feed deprivation and/or during the period of feed deprivation, for instance, during the pre-slaughter period (e.g., may include transport to the slaughter house and/or stay at the slaughter house) or, for instance, before and/or during being transported from one location to another location (which does not necessarily involve slaughtering the livestock animal once it has arrived at the new location).

In an embodiment, the livestock animal may be selected as taught above.

Uses

In a further aspect, use of the compositions as taught herein for preventing or minimizing live body weight loss in a livestock animal (e.g., beef or bull or poultry such as broiler chickens) subjected to a period of feed deprivation is disclosed, for instance, during the pre-slaughter period or during a period surrounding transportation from one location to another location (e.g., before, during and/or after).

In a further aspect, use of the compositions as taught herein for preventing or minimizing carcass weight loss or carcass yield loss following slaughter of a livestock animal subjected to a period of feed deprivation is disclosed, for instance, during the pre-slaughter period or during a period surrounding transportation from one location to another location (e.g., before, during and/or after).

In a further aspect, use of the compositions as taught herein for preventing or minimizing deterioration of the well-being or health of a livestock animal or for improving the well-being or health of a livestock animal subjected to a period of feed deprivation is disclosed, for instance, during the pre-slaughter period or during a period surrounding transportation from one location to another location (e.g., before, during and/or after).

In a further aspect, use of the compositions as taught herein for increasing carcass weight or carcass yield following slaughter of a livestock animal subjected to a period of feed deprivation is disclosed, for instance, during the pre-slaughter period or during a period surrounding transportation from one location to another location (e.g., before, during and/or after).

In a further aspect, use of the compositions as taught herein for preventing or minimizing deterioration of meat quality or for increasing or improving meat quality after slaughter of a livestock animal subjected to a period of feed deprivation is disclosed, for instance, during the pre-slaughter period or during a period surrounding transportation from one location to another location (e.g., before, during and/or after).

In an embodiment, the pre-slaughter period or the periods surrounding transportation (e.g., before, during or after) or the prolonged period of feed deprivation are defined as taught herein.

In an embodiment, the livestock animal may be selected as taught above.

All other teaching and advantages as taught above apply herein.

EXAMPLES

Experiment 1: Effect of Aqueous Compositions with Varying Potassium to Sodium Ratio on Live Body Weight Loss in Holstein Bulls Subjected to a 24-Hour Feed Deprivation Period Goal The goal of this experiment was to assess the effects of varying potassium to sodium ratios on live body weight loss in Holstein bulls subjected to a 24-hour feed deprivation period.

Method

Holstein bulls (n=24), aged 7 months were subjected to a 24-hour feed deprivation period. During the feed deprivation period, the bulls were individually housed in pens measuring 2.5 m×3.5 m. The bulls were individually weighted twice: 1) one hour prior the onset of the feed deprivation period and 2) at the end of the feed deprivation period (i.e., at 24 hours after onset). The percentage of body weight loss in response to 24-hour feed deprivation period (% BW) for each individual bull was calculated as follows:

[(Body weight at onset of feed deprivation−Body weight at the end of feed deprivation)/Body weight at onset of feed deprivation]×100

Treatment

The bulls were divided into three experimental groups as set out in Table 1 below:

TABLE 1

| Experimental groups | | |
|---|---|---|
| | Experimental groups | K:Na ratio |
| 1. | Composition 1 | 75:25 |
| 2. | Composition 2 | 40:60 |
| 3. | Composition 3 | 25:75 |

Compositions

Compositions 1, 2 and 3 were made according to Tables 2, 3, and 4, respectively. Specifically, the ingredients were added in the amounts prescribed into one liter of drinking water. The compositions were stirred using a milk shuttle, at ambient temperature, until all ingredients were dissolved. The total electrolyte osmolarity was 200 mosm/L for compositions 1, 2, and 3.

TABLE 2

| Ingredients of composition 1. | |
|---|---|
| Ingredients | Amounts (g/L of water) |
| Sodium Chloride (NaCl) | 0.30 |
| Sodium Carbonate (NaHCO3) | 1.06 |
| Potassium Chloride (KCl) | 3.88 |
| Magnesium salts from organic acids (MgAc) | 2.43 |

TABLE 3

| Ingredients of composition 2. | |
|---|---|
| Ingredients | Amounts (g/L of water) |
| Sodium Chloride (NaCl) | 1.75 |
| Sodium Carbonate (NaHCO3) | 1.14 |
| Potassium Chloride (KCl) | 2.13 |
| Magnesium salts from organic acids (MgAc) | 2.58 |

TABLE 4

| Ingredients of composition 3. | |
|---|---|
| Ingredients | Amounts (g/L of water) |
| Sodium Chloride (NaCl) | 2.51 |
| Sodium Carbonate (NaHCO3) | 1.14 |
| Potassium Chloride (KCl) | 1.37 |
| Magnesium salts from organic acids (MgAc) | 2.58 |

Experimental Groups

Experimental groups 1, 2, and 3 were offered compositions 1, 2, and 3, respectively, once at the onset of the feed deprivation. Compositions were offered ad libitum in 10-liter buckets (3 per animal) placed in front of the pen. Buckets were re-filled every 4 hours to assure that compositions were available during the entire 24-hour period. Composition intake was measured as follows:

Consumption intake=[weight (kg) of the composition before consumption]−[weight (kg) of the composition after consumption].

Results

The results are depicted in FIG. 1. The results show that bulls that received composition 1 (potassium to sodium ratio of 75:25) lost less live body weight after a 24-hour feed deprivation period than bulls that received composition 2 (potassium to sodium ratio of 40:60) and composition 3 (potassium to sodium ratio of 25:75). The results indicated that electrolyte compositions having a potassium to sodium ratio greater than one work more efficiently at preventing or minimizing feed deprivation-induced live body weight loss than compositions having a potassium to sodium ratio lower than one.

Experiment 2: Effects of Aqueous Compositions with Varying Total Electrolyte Osmolarity on the Live Body Weight of Holstein Bulls Subjected to a 48-Hour Feed Deprivation Period Goal The goal of this experiment was to assess the effects of aqueous compositions having a potassium to sodium ratio greater than one and varying total electrolyte osmolarity on live body weight loss in Holstein bulls subjected to a 48-hour feed deprivation period.

Method

Holstein bulls (n=24), aged 7 months were subjected to a 48-hour feed deprivation period. During the feed deprivation period, the bulls were in individually housed in pens measuring 2.5 m×3.5 m. The bulls were individually weighted twice: 1) one hour prior the onset of the feed deprivation period and 2) at the end of the feed deprivation period (i.e., at 48 hours after onset). The percentage of body weight loss in response to 48-hour feed deprivation period (% BW) for each individual bull was calculated as in experiment 1.

Experimental Groups

The bulls were divided into four experimental groups as set out in Table 5 below:

TABLE 5

Experimental groups

| Experimental groups | K:Na ratio | Total electrolyte osmolarity (mosm/L of drinking water) |
|---|---|---|
| 1. Composition 1 | 00:00 | 0.0 |
| 2. Composition 2 | 75:25 | 100 |
| 3. Composition 3 | 75:25 | 200 |
| 4. Composition 4 | 75:25 | 300 |

Compositions

Compositions 1 (pure water), 2, 3 and 4 were made according to Tables 6, 7, and 8, respectively. Specifically, the ingredients were added in the amounts prescribed into one liter of drinking water. The compositions were stirred using a milk shuttle, at ambient temperature, until all ingredients were dissolved. The potassium to sodium ratio was fixed at 75:25 for all compositions.

TABLE 6

Ingredients of composition 2.

| Ingredients | Amounts (g/L of water) |
|---|---|
| Sodium Chloride (NaCl) | 0.14 |
| Sodium Carbonate (NaHCO3) | 0.50 |
| Potassium Chloride (KCl) | 1.84 |
| Magnesium salts from organic acids (MgAc) | 1.15 |

TABLE 7

Ingredients of composition 3.

| Ingredients | Amounts (g/L of water) |
|---|---|
| Sodium Chloride (NaCl) | 0.30 |
| Sodium Carbonate (NaHCO3) | 1.06 |
| Potassium Chloride (KCl) | 3.88 |
| Magnesium salts from organic acids (MgAc) | 2.43 |

TABLE 8

Ingredients of composition 4.

| Ingredients | Amounts (g/L of water) |
|---|---|
| Sodium Chloride (NaCl) | 0.44 |
| Sodium Carbonate (NaHCO3) | 1.55 |
| Potassium Chloride (KCl) | 5.66 |
| Magnesium salts from organic acids (MgAc) | 3.55 |

Treatment

Experimental groups 1, 2, 3, and 4 were offered compositions 1, 2, 3, and 4 respectively, once at the onset of the feed deprivation.

Results

Figure 2:
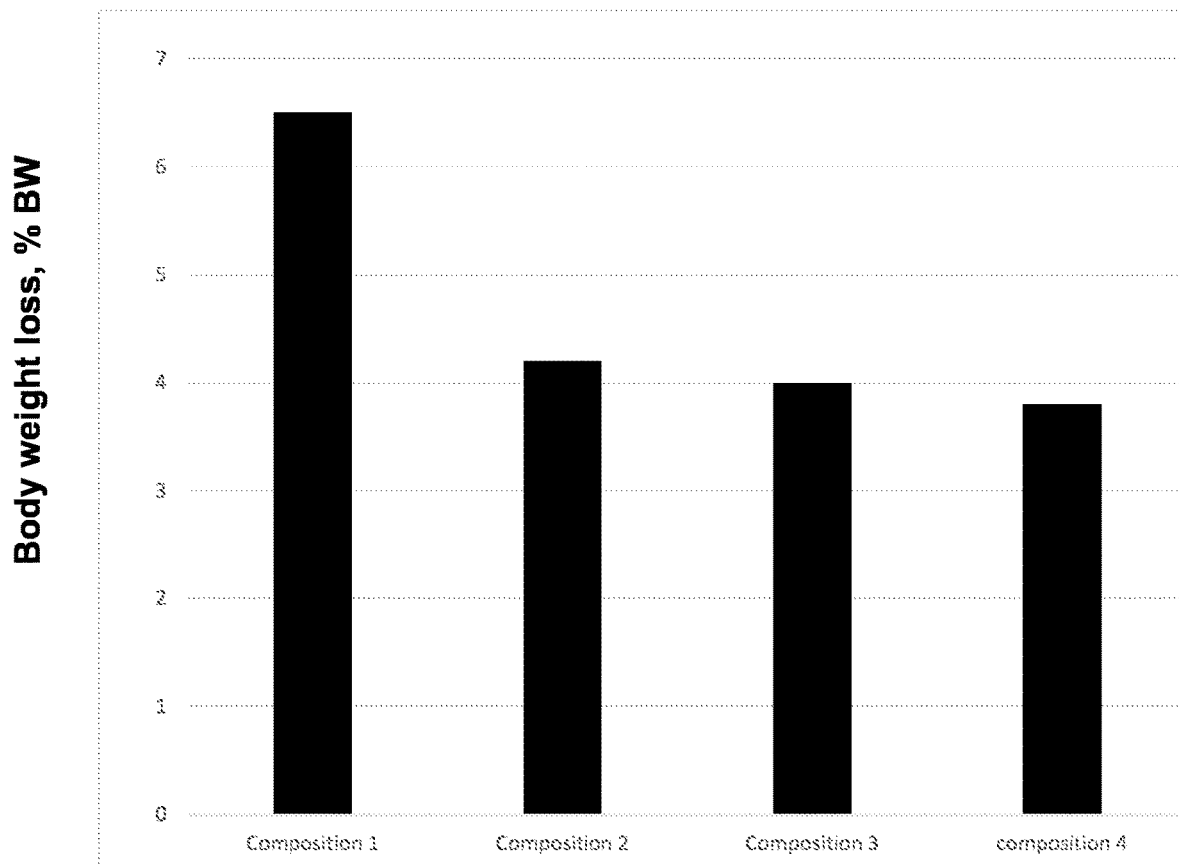
FIG. 2: Effect of aqueous compositions with varying total electrolyte osmolarity on the live body weight of Holstein bulls subjected to a 48-hour feed deprivation period.

The results are depicted in FIG. 2. The results show that bulls that received compositions 1, 2, or 3 (total electrolyte osmolarity of 100, 200, and 300 mosm/L, respectively) lost less live body weight after a 48-hour feed deprivation period than bulls that received composition 1 (total electrolyte osmolarity of 0 mosm/L). The results indicate that compositions having a potassium to sodium ratio greater than one and in which the total electrolytes present in the composition have an osmolarity between 100 and 300 mosm/L, work equally well at preventing or reducing feed deprivation-induced live body weight loss.

Experiment 3: Effect of Aqueous Compositions with Varying Glycerol Levels (%) on the Live Body Weight Loss in Holstein Bulls Subjected to a 48-Hour Feed Deprivation Period Goal The goal of this experiment was to assess whether varying the amount of glycerol in the compositions according to this disclosure (i.e., having a potassium to sodium molar ratio greater than one) influenced the effect of the composition as taught herein on live body weight loss in Holstein bulls subjected to a 48-hour feed deprivation period.

Method

The bulls were subjected to the same experimental conditions as in experiment 2 above. The percentage of body weight loss in response to 48-hour feed deprivation period (% BW) for each individual bull was calculated as in experiment 1.

Experimental Groups

The bulls were divided into three experimental groups as set out in Table 9 below:

TABLE 9

Experimental groups

| Experimental groups | K:Na ratio | osmolarity (mosm/L) | Glycerol (% Vol) |
|---|---|---|---|
| 1. Composition 1 | 75:25 | 200 | 0.0 |
| 2. Composition 2 | 75:25 | 200 | 2.0 |
| 3. Composition 3 | 75:25 | 200 | 4.0 |

Compositions

Compositions 1, 2, and 3 were made according to Table 2 above. An amount of 20 ml/L and 40/L ml of glycerol was added to compositions 2 and 3, respectively. No glycerol was added to composition 1.

Treatment

Experimental groups 1, 2, and were offered compositions 1, 2, and 3, respectively, once at the onset of the feed deprivation. Compositions were offered ad libitum in 10-liter buckets (3 per animal) placed in front of the pen. Buckets were re-filled every 4 hours to assure that compositions were available during the entire 24-hour period. Composition intake was measured as follows:

Consumption intake=[weight (kg) of the composition before consumption]−[weight (kg) of the composition after consumption].

Results

Figure 3:
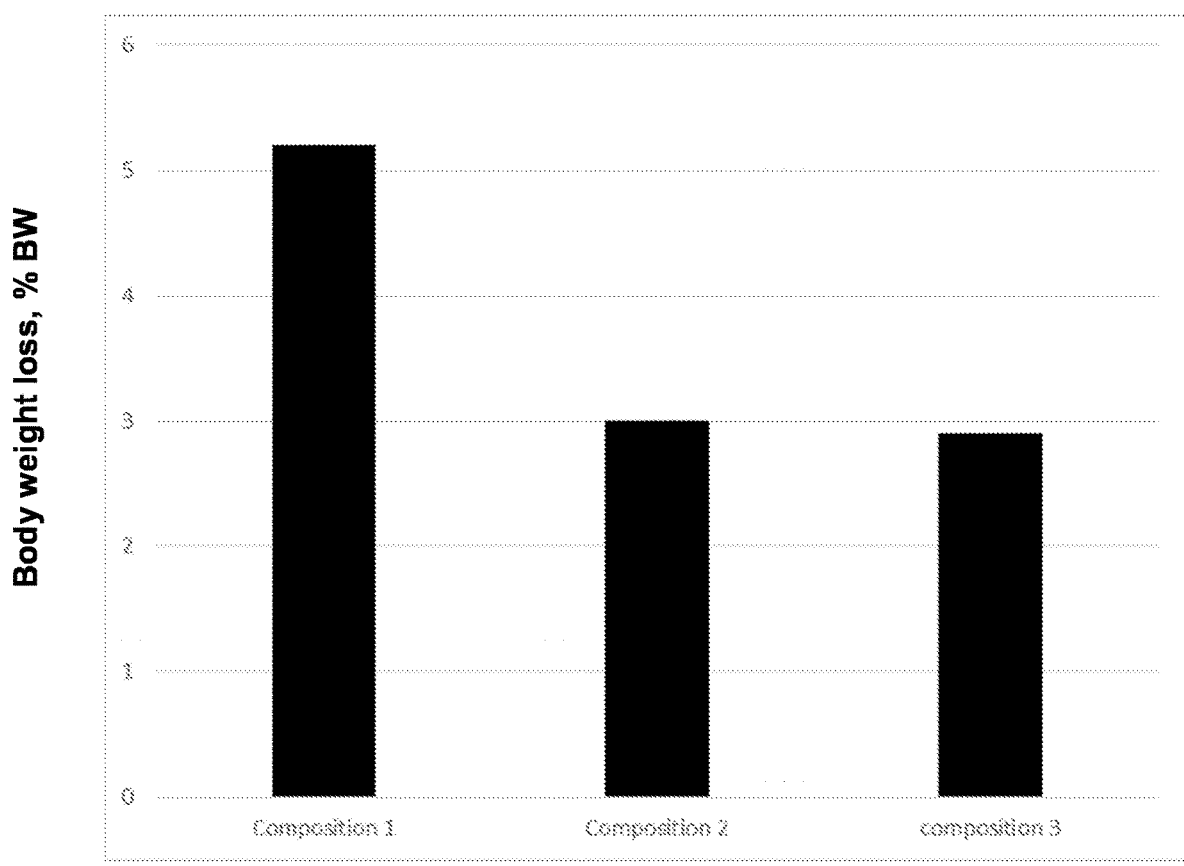
FIG. 3: Effect of aqueous compositions with varying glycerol levels (%) on the live body weight of Holstein bulls subjected to a 48-hour feed deprivation period.

The results are depicted in FIG. 3. The results show that bulls that received compositions 2 or 4 (comprising 2% and 4% glycerol, respectively) lost less live body weight after a 48-hour feed deprivation period than bulls that received composition 1 (comprising 0% glycerol). The results indicate that aqueous compositions having a potassium to sodium ratio greater than one and that further comprise glycerol, work better at preventing or minimizing feed deprivation-induced live body weight loss than compositions having a potassium to sodium ratio greater than one but devoid of glycerol.

Experiment 4. Effect of Aqueous Composition According to the Disclosure on the Live Body Weight Loss and Carcass Weight Post Slaughter, in Holstein Bulls Subjected to a 48-Hour Feed Deprivation Period Goal The goal of this experiment was to compare feed deprivation-induced live body weight loss and carcass weight loss in Holstein bulls administered with the composition as taught herein compared to Holstein bulls administered with drinking water.

Method

Holstein bulls (n=48), aged 8 months were subjected to a 48-hour feed deprivation period. During the feed deprivation period, the bulls were group housed in pens of 2 animals/pen. The percentage of body weight loss in response to 48-hour feed deprivation period (% BW) for each individual bull was calculated as in experiment 1.

Experimental Groups

The bulls were divided into two experimental groups as set out in Table 10 below:

TABLE 10

Experimental groups.

| | Experimental groups | K:Na ratio | osmolarity (mosm/L) | Glycerol (% Vol) |
|---|---|---|---|---|
| 1. | Composition 1 (Pure drinking water) | 0.0 | 0.0 | 0.0 |
| 2. | Composition 2 (aqueous composition) | 75:25 | 200 | 2.0 |

Compositions

Composition 2 was made according to Table 2 above. An amount of 20 ml/L of glycerol was added to composition 2. Composition 1 consisted of pure drinking water.

Treatment

Experimental groups 1 and 2 were offered compositions 1 and 2 respectively, once at the onset of the feed deprivation. Compositions were offered ad libitum in 10-liter buckets (3 per animal) placed in front of the pen. Buckets were re-filled every 4 hours to assure that compositions were available during the entire 48-hour period. Composition intake was measured as follows:

Consumption intake=[weight (kg) of the composition before consumption]−[weight (kg) of the composition after consumption].

Results

Figure 4:
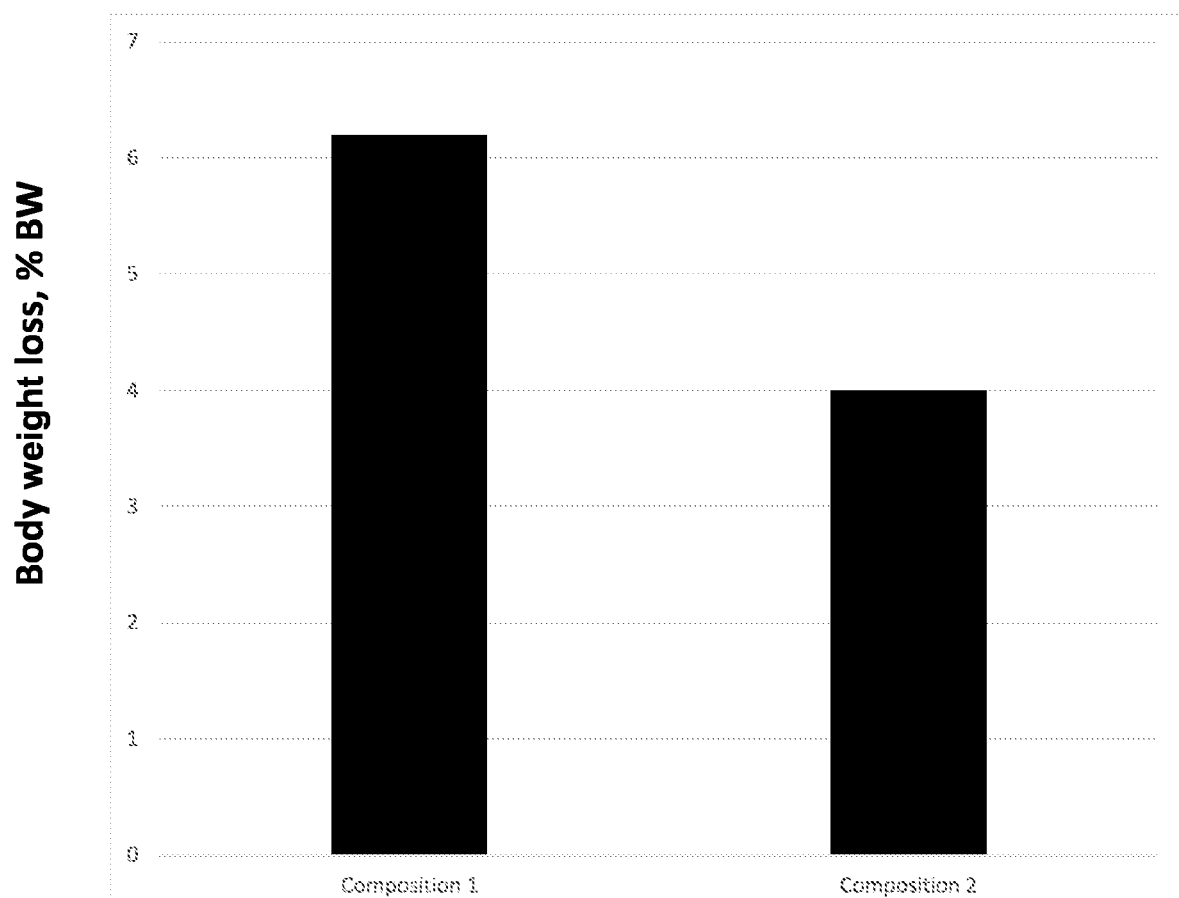
FIG. 4: Effect of the aqueous composition according to this disclosure on the live body weight loss in Holstein bulls subjected to a 48-hour feed deprivation period.
Figure 5:
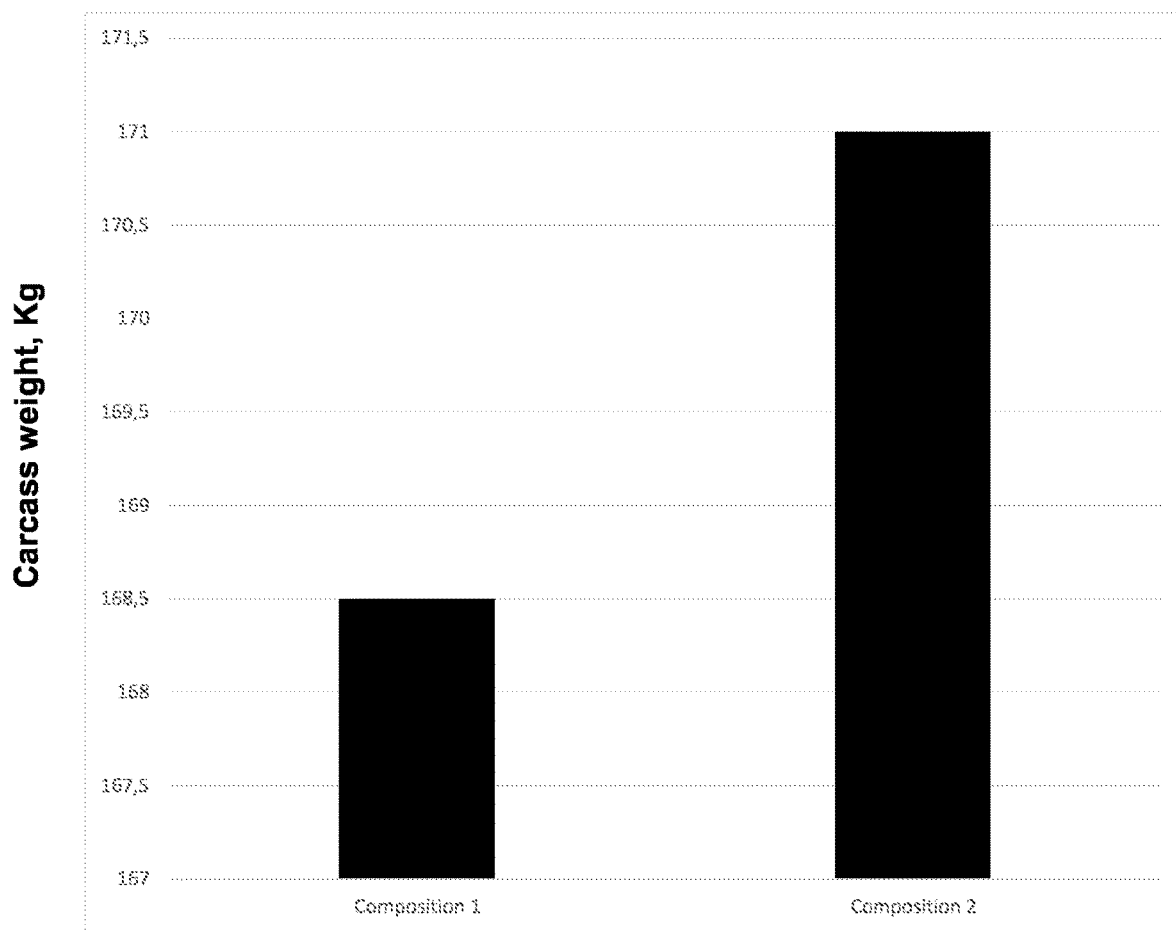
FIG. 5: Effect of the aqueous composition according to this disclosure on carcass weight, post slaughter.

The results are depicted in FIGS. 4 and 5. The results show that bulls that received composition 2 lost less live body weight after a 48-hour feed deprivation period than bulls that received composition 1 (see FIG. 4). The results also show that after slaughter, carcass weight was higher in bulls that received composition 2 prior to slaughter compared to bulls that received composition 1 prior to slaughter (see FIG. 5).

The invention claimed is:

1. A liquid, aqueous composition for a livestock animal, the composition comprising: potassium and sodium, wherein the potassium to sodium ratio is in the range of about 65:35 to about 95:05, and wherein the composition has an osmolarity between about 100 and about 320 mosm/L.

2. The composition according to claim 1, further comprising: one or more electrolytes selected from the group consisting of magnesium, calcium, chloride, bicarbonate, acetate, propionate, sulphate and phosphate.

3. The composition according to claim 2, further comprising one or more gluconeogenic precursor(s).

4. The composition according to claim 3, wherein one or more gluconeogenic precursor(s) is selected from the group consisting of glycerol, propylene glycol, dextrose, lactate, a glucogenic amino acid, and sugar.

5. The composition according to claim 4, wherein the glucogenic amino acid is selected from the group consisting of alanine, glutamine, glycine, serine, valine, histidine, arginine, cysteine, proline, glutamate, aspartate, asparagine, methionine, phenylalanine, isoleucine, threonine, tyrosine and tryptophan.

6. The composition according to claim 5, wherein the glucogenic amino acid is selected from the group consisting of alanine and glutamine.

7. The composition according to claim 4, wherein the sugar is selected from the group consisting of sucrose and maltose.

8. The composition according to claim 1, further comprising an alkalinizing agent.

9. The composition according to claim 8, wherein the alkalinizing agent is selected from the group consisting of propionate, bicarbonate, citrate, carbonate, lactate and acetate anions.

10. A method for preventing or minimizing live body weight loss in a livestock animal subjected to feed deprivation, the method comprising: administering to the livestock animal an effective amount of the composition of claim 1 at the onset of and/or during a period of feed deprivation and/or after a period of feed deprivation has ended.

11. The method according to claim 10, wherein the period of feed deprivation is from about 0.05 to 72 hours.

12. The method according to claim 10, wherein the period of feed deprivation is prior to slaughter of the livestock animal or prior to transportation from one location to another location or during transportation from one location to another location.

13. The method according to claim 10, wherein the livestock animal is selected from the group consisting of ruminants and monogastric animals.

14. The method according to claim 13, wherein the livestock animal is a ruminant selected from the group consisting of bovine, ovine and caprine.

15. The method according to claim 13, wherein the livestock animal is a monogastric animal selected from the group consisting of poultry, swine, and horse.

16. The method according to claim 10, wherein the composition further comprises one or more electrolytes selected from the group consisting of magnesium, calcium, chloride, bicarbonate, acetate, propionate, sulphate and phosphate.

17. The method according to claim 10, wherein the composition further comprises one or more gluconeogenic precursor(s).

18. The method according to claim 17, wherein the one or more gluconeogenic precursor(s) is selected from the group consisting of glycerol, propylene glycol, dextrose, lactate, a glucogenic amino acid, sugar, and glycerol.

19. The method according to claim 18, wherein the one or more gluconeogenic precursor(s) is a glucogenic amino acid selected from the group consisting of alanine, glutamine, glycine, serine, valine, histidine, arginine, cysteine, proline, glutamate, aspartate, asparagine, methionine, phenylalanine, isoleucine, threonine, tyrosine and tryptophan.

20. The method according to claim 19, wherein the glucogenic amino acid is selected from the group consisting of alanine and glutamine.

21. The method according to claim 18, wherein the gluconeogenic precursor is a sugar selected from the group consisting of sucrose and maltose.

22. A method for minimizing carcass weight loss and/or for minimizing meat quality deterioration, the method comprising: administering to a livestock animal an effective amount of the composition of claim 1 within a period of from about 5 to about 72 hours prior to slaughter of the livestock animal, or within a period of about 0.05 to about 72 hours prior to transportation from one location to another location; or within about 0.05 to about 72 hours after transportation from one location to another location; or within a period during transportation from one location to another location.

23. The method according to claim 22, wherein the livestock animal is selected from the group consisting of ruminants and monogastric animals.

24. The method according to claim 23, wherein the livestock animal is a ruminant selected from the group consisting of bovine, ovine, and caprine.

25. The method according to claim 23, wherein the livestock animal is a monogastric animal selected from the group consisting of poultry, swine, and horse.

26. A method for preventing or minimizing deterioration of the well-being or health of a livestock animal, the method comprising: administering to the livestock animal an effective amount of the composition of claim 1 within a period of about 0.05 to about 72 hours prior to transportation of the livestock animal from one location to another location; or within a period of about 0.05 to about 72 hours after transportation from one location to another location; or within a period during transportation from one location to another location.

27. The method according to claim 10, wherein the composition further comprises an alkalinizing agent.

28. The method according to claim 27, wherein the alkalinizing agent is selected from the group consisting of propionate, bicarbonate, citrate, carbonate, lactate, acetate propionate anions, and a mixture of any thereof.

* * * * *